(12) United States Patent
Drysdale et al.

(10) Patent No.: US 6,586,183 B2
(45) Date of Patent: Jul. 1, 2003

(54) ASSOCIATION OF β$_2$-ADRENERGIC RECEPTOR HAPLOTYPES WITH DRUG RESPONSE

(75) Inventors: Connie M. Drysdale, Branford, CT (US); Richard S. Judson, Guilford, CT (US); Stephen B. Liggett, Cincinnati, OH (US); Krishnan Nandabalan, Guilford, CT (US); Catherine B. Stack, Old Saybrook, CT (US); J. Claiborne Stephens, Guilford, CT (US)

(73) Assignee: Genaissance Pharmaceuticals, Inc., New Haven, CT (US)

( * ) Notice: Subject to any disclaimer, the term of this patent is extended or adjusted under 35 U.S.C. 154(b) by 0 days.

(21) Appl. No.: 09/811,286

(22) Filed: Mar. 16, 2001

(65) Prior Publication Data

US 2001/0051712 A1 Dec. 13, 2001

Related U.S. Application Data

(63) Continuation of application No. PCT/US00/10125, filed on Apr. 13, 2000.

(51) Int. Cl.$^7$ .......................... C07H 21/04; C12Q 1/68; C12P 19/34
(52) U.S. Cl. ..................... 435/6; 435/91.1; 435/91.2; 536/23.5
(58) Field of Search .................... 435/6, 91.2, 91.1; 536/23.5

(56) References Cited

U.S. PATENT DOCUMENTS 6,156,503 A * 12/2000 Drazen et al. ............... 435/6

FOREIGN PATENT DOCUMENTS

| WO | WO 98/39477 A2 | 9/1998 |
|----|----------------|--------|
| WO | WO 99/37761 A1 | 7/1999 |
| WO | WO 00/31307 A1 | 6/2000 |
| WO | WO 01/06910 A2 | 2/2001 |

OTHER PUBLICATIONS

Liggett, S., "B–Adrenergic Receptor Polymorphisms", Pending U.S. Application Ser. No. 08/948,643, (Filed Oct. 10, 1997).

Liggett, S.B., "Polymorphisms in the 5' Leader Cistron of the B2–Adrenergic Receptor," Pending U.S. Application, Ser. No. 09/856,803, (Filed May 25, 2001).

Green, S.A., "Amino–Terminal Polymorphisms of the Human B2–Adrenergic Receptor Impart Distinct Agonist–Promoted Regulatory Properties," Biochemistry, vol. 33, p. 9414–9419, 1994.

D'Amato, Mauro et al., "Association of Persistent Bronchial Hyperresponsiveness with B2–Adrenergic (ADRB2) Haplotypes," Am. J. Respir. Crit. Care. Med, vol. 158 (No. 1), p. 1968–1973, 1998.

Hancox, R.J. et al., "Polymorphism of the B2–Adrenoceptor and the Response to long–term B2–Agonist Therapy in Asthma," Eur. Respir. J., vol. 11 (No. 1), p. 589–593, 1998.

Lima, John J. et al., "Impact of Genetic Polymorphisms of the B2–Adrenergic Receptor on Albuterol Bronchodilator Pharmacodynamics," Clinical Pharmacology & Therapeutics, vol. 68 (No. 5), p. 519–525, 1999.

Lipworth, B.J. et al., "B2–Adrenoceptor Polymorphism and Bronchoprotective Sensitivity with Regular Short–and Long–Acting B2–agonist Therapy," Clinical Science, vol. 96 (No. 1), p. 253–259, 1999.

Martinez, Fernando D. et al., "Association Between Genetic Polymorphisms of the B2–Adrenoceptor and Response to Albuterol in Children With and Without a History of Wheezing," J. Clin. Invest., vol. 100 (No. 12), p. 3184–3188, 1997.

McGraw, Dennis W. et al., "Polymorphisms of the 5' Leader Cistron of the Human B2–Adrenergic Receptor Regulate Receptor Expression," J. Clin. Invest., vol. 102 (No. 11), p. 1927–1932, 1998.

Reihsaus, Ellen et al., "Mutations in the Gene Encoding for the B2–Adrenergic Receptor in Normal and Asthmatic Subjects," Am. J. Respir. Cell. Mol. Biol., vol. 8(No. 1), p. 334–339, 1993.

Scott, Mark G.H. et al., "Identification of Novel Polymorphisms within the Promoter Region of the Human B2–Adrenergic Receptor Gene," British Journal of Pharmacology, vol. 126 (No. 1), p. 841–844, 1999.

Timmermann, Bernd et al., "B–2 Adrenoceptor Genetic Variation is Associated with Genetic Predisposition to Essential Hypertension; The Bergen Blood Pressure Study," Kidney International, vol. 53 (No. 1), p. 1455–1460, 1998.

Weir, Tracey D. et al., "B2–Adrenergic Receptor Haplotypes in Mild, Moderate and Fatal/Near Fatal Asthma," Am. J. Respir. Crit. Care. Med., vol. 158 (No. 1), p. 787–791, 1998.

* cited by examiner

Primary Examiner—Yvonne Eyler
Assistant Examiner—Joseph F. Murphy
(74) Attorney, Agent, or Firm—Gisela F. Carlson; Melodie W. Henderson

(57) ABSTRACT

Genotypes and haplotypes for thirteen polymorphic sites in the β$_2$-adrenergic receptor (β$_2$AR) gene are disclosed. Compositions and methods for predicting genetic predisposition to disease associated with polymorphic sites in the (β$_2$AR) gene, as well as for predicting response to β-agonists, are also disclosed.

10 Claims, 8 Drawing Sheets

POLYMORPHISMS IN THE BETA-2-ADRENERGIC RECEPTOR GENE

```
CCCGGGTTCA AGAGATTCTC CTGTCTCAGC CTCCCGAGTA GCTGGGACTA
CAGGTACGTG CCACCACACC TGGCTAATTT TTGTATTTTT AGTAGAGACA        100
AGAGTTACAC CATATTGGCC AGGATCTTTT GCTTTCTATA GCTTCAAAAT
GTTCTTAATG TTAAGACATT CTTAATACTC TGAACCATAT GAATTTGCCA        200
TTTTGGTAAG TCACAGACGC CAGATGGTGG CAATTTCACA TGGCACAACC
CGAAAGATTA ACAAACTATC CAGCAGATGA AAGGATTTTT TTTAGTTTCA        300
TTGGGTTTAC TGAAGAAATT GTTTGAATTC TCATTGCATC TCCAGTTCAA
CAGATAATGA GTGAGTGATG CCACACTCTC AAGAGTTAAA AACAAAACAA        400
CAAAAAAATT AAAACAAAAG CACACAACTT TCTCTCTCTG TCCCAAAATA
CATACTTGCA TACCCCGCT  CCAGATAAAA TCCAAAGGGT AAAACTGTCT        500
TCATGCCTGC AAATTCCTAA GGAGGGCACC TAAAGTACTT GACAGCGAGT
GTGCTGAGGA AATCGGCAGC TGTTGAAGTC ACCTCCTGTG CTCTTGCCAA        600
                A
ATGTTTGAAA GGGAATACAC TGGGTTACCG GGTGTATGTT GGGAGGGGAG
CATTATCAGT GCTCGGGTGA GGCAAGTTCG GAGTACCCAG ATGGAGACAT        700
CCGTGTCTGT GTCGCTCTGG ATGCCTCCAA GCCAGCGTGT GTTTACTTTC
TGTGTGTGTC ACCATGTCTT TGTGCTTCTG GGTGCTTCTG TGTTTGTTTC        800
TGGCCGCGTT TCTGTGTTGG ACAGGGGTGA CTTTGTGCCG GATGGCTTCT
GTGTGAGAGC GCGCGCGAGT GTGCATGTCG GTGAGCTGGG AGGGTGTGTC        900
                                A
TCAGTGTCTA TGGCTGTGGT TCGGTATAAG TCTGAGCATG TCTGCCAGGG
                                     A
TGTATTTGTG CCTGTATGTG CGTGCCTCGG TGGGCACTCT CGTTTCCTTC       1000
CGAATGTGGG GCAGTGCCGG TGTGCTGCCC TCTGCCTTGA GACCTCAAGC
CGCGCAGGCG CCCAGGGCAG GCAGGTAGCG GCCACAGAAG AGCCAAAAGC       1100
TCCCGGGTTG GCTGGTAAGG ACACCACCTC CAGCTTTAGC CCTCTGGGGC
                                              C
CAGCCAGGGT AGCCGGGAAG CAGTGGTGGC CCGCCCTCCA GGGAGCAGTT       1200
                                    T
GGGCCCCGCC CGGGCCAGCC CCAGGAGAAG GAGGGCGAGG GGAGGGGAGG
                      T
GAAAGGGGAG GAGTGCCTCG CCCCTTCGCG GCTGCCGGCG TGCCATTGGC       1300
CGAAAGTTCC CGTACGTCAC GGCGAGGGCA GTTCCCCTAA AGTCCTGTGC
ACATAACGGG CAGAACGCAC TGCGAAGCGG CTTCTTCAGA GCACGGGCTG       1400
GAACTGGCAG GCACCGCGAG CCCCTAGCAC CCGACAAGCT GAGTGTGCAG
GACGAGTCCC CACCACACCC ACACCACAGC CGCTGAATGA GGCTTCCAGG       1500
CGTCCGCTCG CGGCCCGCAG AGCCCCGCCG TGGGTCCGCC CGCTGAGGCG
                                              T
```

Figure 1A

```
CCCCCAGCCA GTGCGCTTAC CTGCCAGACT GCGCGCCATG GGGCAACCCG    1600
                 C
GGAACGGCAG CGCCTTCTTG CTGGCACCCA ATAGAAGCCA TGCGCCGGAC
                              G
CACGACGTCA CGCAGCAAAG GGACGAGGTG TGGGTGGTGG GCATGGGCAT    1700
         G
CGTCATGTCT CTCATCGTCC TGGCCATCGT GTTTGGCAAT GTGCTGGTCA
TCACAGCCAT TGCCAAGTTC GAGCGTCTGC AGACGGTCAC CAACTACTTC    1800
ATCACTTCAC TGGCCTGTGC TGATCTGGTC ATGGGCCTGG CAGTGGTGCC
                                         A
CTTTGGGGCC GCCCATATTC TTATGAAAAT GTGGACTTTT GGCAACTTCT    1900
GGTGCGAGTT TTGGACTTCC ATTGATGTGC TGTGCGTCAC GGCCAGCATT
GAGACCCTGT GCGTGATCGC AGTGGATCGC TACTTTGCCA TTACTTCACC    2000
TTTCAAGTAC CAGAGCCTGC TGACCAAGAA TAAGGCCCGG GTGATCATTC
TGATGGTGTG GATTGTGTCA GGCCTTACCT CCTTCTTGCC CATTCAGATG    2100
                                              T
CACTGGTACC GGGCCACCCA CCAGGAAGCC ATCAACTGCT ATGCCAATGA
   A
GACCTGCTGT GACTTCTTCA CGAACCAAGC CTATGCCATT GCCTCTTCCA    2200
TCGTGTCCTT CTACGTTCCC CTGGTGATCA TGGTCTTCGT CTACTCCAGG
GTCTTTCAGG AGGCCAAAAG GCAGCTCCAG AAGATTGACA AATCTGAGGG    2300
CCGCTTCCAT GTCCAGAACC TTAGCCAGGT GGAGCAGGAT GGGCGGACGG
GGCATGGACT CCGCAGATCT TCCAAGTTCT GCTTGAAGGA GCACAAAGCC    2400
CTCAAGACGT TAGGCATCAT CATGGGCACT TTCACCCTCT GCTGGCTGCC
CTTCTTCATC GTTAACATTG TGCATGTGAT CCAGGATAAC CTCATCCGTA    2500
AGGAAGTTTA CATCCTCCTA AATTGGATAG GCTATGTCAA TTCTGGTTTC
AATCCCCTTA TCTACTGCCG GAGCCCAGAT TTCAGGATTG CCTTCCAGGA    2600
GCTTCTGTGC CTGCGCAGGT CTTCTTTGAA GGCCTATGGG AATGGCTACT
CCAGCAACGG CAACACAGGG GAGCAGAGTG GATATCACGT GGAACAGGAG    2700
AAAGAAAATA AACTGCTGTG TGAAGACCTC CCAGGCACGG AAGACTTTGT
GGGCCATCAA GGTACTGTGC CTAGCGATAA CATTGATTCA CAAGGGAGGA    2800
ATTGTAGTAC AAATGACTCA CTGCTGTAAA GCAGTTTTTC TACTTTTAAA
GACCCCCCCC CCCCCAACAG AACACTAAAC AGACTATTTA ACTTGAGGGT    2900
AATAAACTTA GAATAAAATT GTAAAAATTG TATAGAGATA TGCAGAAGGA
AGGGCATCCT TCTGCCTTTT TTATTTTTTT AAGCTGTAAA AAGAGAGAAA    3000
ACTTATTTGA GTGATTATTT GTTATTTGTA CAGTTCAGTT CCTCTTTGCA
TGGAATTTGT AAGTTTATGT CTAAAGAGCT TTAGTCCTAG AGGACCTGAG    3100
TCTGCTATAT TTTCATGACT TTTCCATGTA TCTACCTCAC TATTCAAGTA
TTAGGGGTAA TATATTGCTG CTGGTAATTT GTATCTGAAG GAGATTTTCC    3200
TTCCTACACC CTTGGACTTG AGGATTTTGA GTATCTCGGA CCTTTCAGCT
```

Figure 1B

```
GTGAACATGG ACTCTTCCCC CACTCCTCTT ATTTGCTCAC ACGGGGTATT      3300
TTAGGCAGGG ATTTGAGGAG CAGCTTCAGT TGTTTTCCCG AGCAAAGGTC
TAAAGTTTAC AGTAAATAAA ATGTTTGACC ATGCCTTCAT TGCACCTGTT      3400
TGTCCAAAAC CCCTTGACTG GAGTGCTGTT GCCTCCCCCA CTGGAAACCG
C                                                           3451
```

Figure 1C

ISOFORMS OF BETA-2-ADRENERGIC RECEPTOR (ADRB2)

```
MGQPGNGSAF LLAPNRSHAP DHDVTQQRDE VWVVGMGIVM SLIVLAIVFG
                G          E
NVLVITAIAK FERLQTVTNY FITSLACADL VMGLAVVPFG AAHILMKMWT        100
FGNFWCEFWT SIDVLCVTAS IETLCVIAVD RYFAITSPFK YQSLLTKNKA
RVIILMVWIV SGLTSFLPIQ MHWYRATHQE AINCYANETC CDFFTNQAYA        200
                I
IASSIVSFYV PLVIMVFVYS RVFQEAKRQL QKIDKSEGRF HVQNLSQVEQ
DGRTGHGLRR SSKFCLKEHK ALKTLGIIMG TFTLCWLPFF IVNIVHVIQD        300
NLIRKEVYIL LNWIGYVNSG FNPLIYCRSP DFRIAFQELL CLRRSSLKAY
GNGYSSNGNT GEQSGYHVEQ EKENKLLCED LPGTEDFVGH QGTVPSDNID        400
SQGRNCSTND SLL                                                413
```

FIGURE 2

ASSOCIATION OF β₂-ADRENERGIC RECEPTOR HAPLOTYPES WITH DRUG RESPONSE

CROSS REFERENCE TO RELATED APPLICATION

This Application is a continuation of PCT/US00/10125 filed Apr. 13, 2000.

FIELD OF THE INVENTION

This invention relates to the fields of genomics and pharmacogenetics. More specifically, the present invention relates to polymorphisms and haplotypes of the $\beta_2$-adrenergic receptor gene and their use as predictors of disease susceptibility and response to β-agonists.

BACKGROUND OF THE INVENTION

The $\beta_2$-adrenergic receptor ($\beta_2AR$) is a G protein coupled receptor that mediates the actions of catecholamines in multiple tissues and thus plays important roles in regulating cardiac, vascular, pulmonary, and metabolic functions. An abnormal level of expression of $\beta_2AR$ is believed to be a risk factor for or to modify the severity of a number of diseases and conditions, including congestive heart failure, arrhythmia, ischemic heart disease, hypertension, migraine, asthma, chronic obstructive pulmonary disease (COPD), anaphylaxis, obesity, diabetes, myasthenia gravis, and premature labor.

The $\beta_2AR$ is encoded by an intronless gene on chromosome 5q31-32 Kobilka, B. K. et al., *Proc. Natl. Acad. Sci., USA* 84:46-50, 1987). Several single nucleotide polymorphisms (SNPs) in the coding block of the $\beta_2AR$ gene that lead to significant genetic variability in the structure of the $\beta_2AR$ protein in the human population have been reported (Reihsaus, E. et al., *Am J Resp Cell Mol Biol* 8:334-339, 1993; Liggett, S. B., *News in Physiologic Sciences* 10:265-273, 1995; and GenBank accession numbers AF022953.1 GI:2570526; AF022954.1 GI:2570528; and AF022956.1 GI:2570532). These SNPs are located at nucleotides 46 (A or G), 79 (C or G), and 491 (C or T) of the $\beta_2AR$ coding sequence, and result in variation that occurs in the amino-terminus of the receptor at amino acids 16 (Arg or Gly) and 27 (Gln or Glu) and in the fourth transmembrane spanning domain at amino acid 164 (Thr or Ile), respectively. These amino acid variants have clear phenotypic differences as demonstrated by recombinant cell studies (Green, S. A. et al., *Biochem* 33:9414-9419, 1994; Green, S. A., et al., *J Biol Chem* 268:23116-23121, 1993), primary cultures of cells endogenously expressing these variants (Green, S. A., et al., *Am J Resp Cell Mol Biol* 13:25-33, 1995), and transgenic mice overexpressing the Thr164 or Ile164 receptors in the heart (Turki et al., *Proc. Nat. Acad. Sci., USA* 93:10483-10488, 1996). In addition, a synonymous polymorphism of C or A at nucleotide 523 in the coding sequence has been reported to be associated with altered responsiveness to salbutamol in Japanese families (Ohe, M. et al., *Thorax* 50:353-359, 1995).

In addition to the above polymorphisms in the coding block, several SNPs in the 5' promoter region have recently been identified and are located at nucleotides −1023 (A or G), −654 G or A), −468 (C or G), −367 (T or C), −47 (C or T) and −20 (T or C) (Scott, M. G. H. et al., *Br J Pharmacol* 126:841-844, 1999). Thus, eleven polymorphic sites have previously been identified in the region of the $\beta_2AR$ gene located between nucleotides 565 and 2110 of GenBank Accession No. M15169.1 (see FIG. 1 (SEQ ID NO:1)).

Messenger RNA transcripts of the $\beta_2AR$ gene have a 5' leader region harboring a short open reading frame (ORF), termed the $\beta_2AR$ 5'-leader cistron (5'LC), that encodes a 19 amino acid peptide (Kobilka, B. K. et al., *J. Biol. Chem.:* 262:7321-7327, 1996). This $\beta_2AR$ upstream peptide (BUP) modulates translation of $\beta_2AR$ mRNA, and thereby regulates cellular expression of the receptor (Parola, A. L. et al., *J Biol Chem* 269:4497-4505, 1994). The polymorphic site located at −47, described above, is in this 5'LC and results in either Arg or Cys being encoded at the terminal amino acid position 19) of the BUP. It was recently reported that the Cys19 variant of the BUP is associated with greater $\beta_2AR$ expression than the Arg19 BUP variant (McGraw et al., *J. Clin. Invest.* 102:1927-1932, 1998).

Several groups have suggested associations between some of the above $\beta_2AR$ amino acid variants and increased susceptibility to various conditions, including: high blood pressure (Gly16 variant, Hoit et al., *Am Heart J* 139:537-542, 2000; Gratze et al., *Hypertension* 33:1425-1430, 1999 and Kotanko, P. et al., *Hypertension* 30:773-776, 1997; cf. Arg16 variant, Busjahn et al., *Hypertension* 35:555-560, 2000); atopy (Gly16 variant, Dewar et al., *Clin. Exp. Allergy* 28:442-448, 1998); nocturnal asthma (Gly16 variant, Turki et al., *J. Clin. Invest.* 95:1635-1641, 1995); response to treatment for obesity (Gly16 variant, Sakane et al., *Lancet* 353:1976, 1999); myasthenia gravis (Arg16 variant, Xu, B. -Y. et al., *Clin. & Exp. Immunol.* 119:156-160, 2000); childhood asthma (Gln27 variant, Dewar et al., *J. Allergy Clin. Immun.* 100:261-265, 1997); obesity (Glu27 variant, Large et al., *J. Clin. Invest.* 100:3005-3013, 1997); and mortality from congestive heart failure (Ile164 variant, Liggett et al., *J. Clin. Invest.* 102:1534-1539, 1998).

Several of the polymorphic sites (PS) in the $\beta_2AR$ gene have been reported to be in linkage disequilibrium with each other, including between the +46 and +79 PS (Martinez et al., *J. Clin. Invest.* 100:261-265, 1997; Dewar et al., supra), between the −47, +46 and +79 PS (McGraw et al., supra), between the −47, −20, +46, and +79 PS (Yamada et al., *J. Clin. Endocrinol. Metab.* 84:1754-1757, 1999), and between the +79 and +523 PS (Dewar et al., *Clin. and Exp. Allergy* 28:442-448, 1998). In addition, associations between various in vivo phenotypes and haplotypes for various combinations of these polymorphic sites have been suggested: obesity and a −47 C/−20 C haplotype (Yamada et al., supra), asthma severity and a +46G/+79G haplotype (which encodes the Gly16/Gln27 variant) (Weir et al., *Am J. Resp. Crit Care Med.* 158:787-791, 1998); bronchial hyperresponsiveness (BHR) and a +46 G/+79 G haplotype (D'amato et al., *Am. J. Resp. Crit. Care Med.* 158:1968-1973, 1998); hypertension and a −47 T/+46 A/+79 C haplotype, and the following expanded version thereof: −1023 G/−654 A/−47 T/−20 C/+46 A/+79 C (Timmerman et al. *Kidney Int.* 53:1455-1460, 1998; WO 99/37761). An association between reduced $\beta_2AR$ promoter activity in vitro and a haplotype of −468 G/−367 C/−47 C/−20 C has also been reported (Scott et al., *Br. J. Pharmacol.* 126:841-844, 1999). However, no haplotypes covering more than six of the above 11 sites have been reported.

It has also been suggested that some of the $\beta_2AR$ gene polymorphisms discussed above may act as disease modifiers in asthma or may be the basis for the known interindividual variation in the bronchodilating response to β-agonists (Liggett, S. B. "The genetics of $\beta_2$-adrenergic receptor polymorphisms: relevance to receptor function and asthmatic phenotypes." in: Liggett, S. B. & Meyers, D. A., *The Genetics of Asthma* (1996) pp. 455-478). Indeed, two groups have reported that individuals homozygous or heterozygous for the Arg16 variant are more likely to respond to albuterol than individuals homozygous for the Gly16 variant. (Martinez, F. D. et al., *J Clin Invest* 100:3184–3188, 1997 and Lima, J. J., et al., *Clin Pharmacol Ther* 65:519–525, 1999). It has also been reported that asthmatic individuals who are homozygous for the Arg16 variant are more likely to exhibit decreased response to repeated use of albuterol (Drazen et al., WO 98/39477). Interestingly, another group reported bronchodilator desensitization in asthmatics homozygous for the Gly16 variant following continuous therapy with the β-agonist formoterol (Tan et al., *Lancet* 350:995–999, 1997). Other studies failed to demonstrate any correlations between adverse drug response and regular treatment with β-agonists (Hancox, R. J. et al., *Eur Respir J* 11:589–593, 1998; Lipworth, B. J. et al., *Clinical Science* 96:253–259, 1999). Moreover, none of the human physiologic studies assessed the relevance of haplotypes of multiple $\beta_2AR$ polymorphisms in both the promoter and coding regions for predicting the bronchodilator response to β-agonists. Also, the phylogeny of these haplotypes and their distribution amongst different ethnic groups, which has particular relevance to pharmacogenetics, has not been explored.

Because of the potential for individual polymorphisms and haplotypes in the $\beta_2AR$ gene to affect susceptibility to a number of diseases, as well as affect response to β-agonist therapy, it would be useful to determine whether additional polymorphisms exist in the $\beta_2AR$ gene, how such polymorphisms are combined in different copies of the gene to (haplotypes), and whether the frequencies of such polymorphisms and haplotypes vary among different ethnic groups. Such information would be useful for studying the biological function of $\beta_2AR$ as well as in identifying drugs targeting $\beta_2AR$ for the treatment of disorders related to its abnormal expression or function.

SUMMARY OF THE INVENTION

Accordingly, the inventors herein have discovered two novel polymorphic sites in the $\beta_2AR$ gene. These polymorphic sites (PS) correspond to the nucleotide positions 879 and 1182 in the promoter region of the $\beta_2AR$ gene (see FIG. 1) and are designated PS2 and PS5, respectively, to reflect their order in the $\beta_2AR$ gene relative to the other 11 polymorphic sites (Table 3). The polymorphisms at these sites are cytosine or adenine at PS2 and cytosine or thymine at PS5. It is believed that $\beta_2AR$-encoding polynucleotides containing one or more of these novel polymorphic sites will be useful in studying the expression and biological function of $\beta_2AR$, as well as in developing drugs targeting this receptor.

In addition, the inventors have determined the identity of the alternative nucleotides present at these sites, and at the previously identified 11 polymorphic sites described above (see Table 3), in a human reference population of apparently normal unrelated individuals representing four major population groups and in a cohort of asthma patients. The inventors herein have also identified how the polymorphisms at these 13 polymorphic sites in the $\beta_2AR$ gene (see FIG. 1) are combined into haplotypes in the reference and patient populations (see Tables 4 and 5) and discovered that certain pairs of these haplotypes, designated 2/2, 2/4, 2/6, 4/4 and 4/6 are predictive of bronchodilator response to albuterol. Asthmatic patients having β2 haplotype pairs 2/2 and 4/6 respond well to albuterol while patients with $\beta_2AR$ haplotype pairs 2/4 and 4/4 exhibit little to no response. $\beta_2AR$ haplotype pair 2/6 is associated with a moderate bronchodilator response. The inventors herein have also discovered that the presence of one of these medically significant haplotype pairs in an asthma patient may be predicted with high confidence by genotyping only three sites: PS3, PS9 and PS11.

Thus, in one embodiment, the invention provides an isolated polynucleotide comprising a nucleotide sequence which is a polymorphic variant of a reference sequence for the $\beta_2AR$ gene or a fragment thereof. The reference sequence comprises SEQ ID NO:1 and the polymorphic variant comprises at least one polymorphism selected from the group consisting of adenine at PS2 and thymine at PS5. A particularly preferred polymorphic variant is a naturally-occurring isoform (also referred to herein as an "isogene") of the $\beta_2AR$ gene. A $\beta_2AR$ isogene of the invention comprises guanine or adenine at PS1, cytosine or adenine at PS2, guanine or adenine at PS3, guanine or cytosine at PS4, cytosine or thymine at PS5, cytosine or thymine at PS6, cytosine or thymine at PS7, thymine or cytosine at PS8, adenine or guanine at PS9, cytosine or guanine at PS10, guanine or adenine at PS11, cytosine or thymine at PS12, and cytosine or adenine at PS13. The invention also provides a collection of $\beta_2AR$ isogenes, referred to herein as a $\beta_2AR$ genome anthology.

A $\beta_2AR$ isogene may be defined by the combination and order of these polymorphisms in the isogene, which is referred to herein as a $\beta_2AR$ haplotype. Thus, the invention also provides data on the number of different $\beta_2AR$ haplotypes found in the above four population groups. This haplotype data is useful in methods for deriving a $\beta_2AR$ haplotype from an individual's genotype for the $\beta_2AR$ gene and for determining an association between a $\beta_2AR$ haplotype and a particular trait.

In another embodiment, the invention provides a recombinant expression vector comprising one of the polymorphic $\beta_2AR$ genomic variants operably linked to expression regulatory elements as well as a recombinant host cell transformed or transfected with the expression vector. The recombinant vector and host cell may be used to express $\beta_2AR$ for protein structure analysis and drug binding studies.

The invention also provides methods, compositions, and kits for haplotyping and/or genotyping the $\beta_2AR$ gene in an individual. In one embodiment, the genotyping method comprises isolating from the individual a nucleic acid mixture comprising the two copies of the $\beta_2AR$ gene present in the individual and determining the identity of the nucleotide pair at one or both of PS2 and PS5 in the two copies to assign a $\beta_2AR$ genotype to the individual. In another embodiment, a method for predicting an individuals haplotype pair comprises determining the individuals genotype at PS3, PS9 and PS11. The compositions contain oligonucleotide probes or primers designed to specifically hybridize to one or more target regions containing, or that are adjacent to, one or both of PS2 and PS5. Kits of the invention comprise a set of oligonucleotides for genotyping at least PS3, PS9 and PS11 and may also comprise additional oligonucleotides for genotyping one or more additional polymorphic sites selected from the group consisting of PS1, PS2, PS4, PS5, PS6, PS7, PS8, PS10, PS12 and PS13. The methods and compositions for genotyping or haplotyping PS2 and PS5 in the $\beta_2AR$ gene are useful for studying the effect of the alternative nucleotides at PS2 and PS5 in the etiology of various diseases and efficacy of drugs targeting the $\beta_2AR$. Methods and kits for genotyping and haplotyping PS3, PS9 and PS11 are useful for predicting an asthmatic patient's bronchodilating response to β-agonists.

In yet another embodiment, the invention provides a method for identifying an association between a $\beta_2AR$ haplotype and a trait. In preferred embodiments, the trait is susceptibility to a disease, disease severity, the staging of a disease or response to a drug. Such methods have applicability in developing diagnostic tests and therapeutic treatments for one or more conditions selected from the group consisting of congestive heart failure, arrhythmia, ischemic heart disease, hypertension, migraine, asthma, chronic obstructive pulmonary disease (COPD), anaphylaxis, obesity, diabetes, myasthenia gravis (MG) and premature labor. In other preferred embodiments, the drug is an agonist or antagonist of $\beta_2AR$.

The present invention also provides genetically modified animals comprising one or more of the novel $\beta_2AR$ genomic polymorphic variants described herein and methods for producing such animals. Such animals are useful for studying expression of the $\beta_2AR$ isogenes in vivo, for in vivo screening and testing of drugs targeted against $\beta_2AR$ protein, and for testing the efficacy of therapeutic agents and compounds targeting the $\beta_2AR$ in a biological system.

The present invention also provides a computer system for storing and displaying polymorphism data determined for the $\beta_2AR$ gene. The computer system comprises a computer processing unit; a display; and a database containing the polymorphism data. The polymorphism data includes the polymorphisms, the genotypes and the haplotypes identified for the $\beta_2AR$ gene in one or both of the reference population and the patient population. In a preferred embodiment, the computer system is capable of producing a display showing $\beta_2AR$ haplotypes organized according to their evolutionary relationships.

Another aspect of the invention is based on the discovery of novel information relating to linkage disequilibrium in Caucasians between PS1, PS3, PS4 and PS6 and the $\beta_2AR$ polymorphic sites previously reported to be associated with various medical conditions, i.e., PS9 and PS10. Thus, the present invention also provides a method for predicting a Caucasian individual's genetic predisposition to any disease or condition known to be associated with one of the alternative alleles at PS9 or PS10 in the $\beta_2AR$ gene. The method comprises determining a first genotype for a first polymorphic site in the individual's $\beta_2AR$ gene, wherein the first polymorphic site is selected from the group consisting of PS1, PS3, PS4 and PS6, and using the first genotype to predict a second genotype for a second polymorphic site in the individual's $\beta_2AR$ gene, wherein if the first polymorphic site is PS1, PS4 or PS6, then the second polymorphic site is PS10, and if the first polymorphic site is PS3, then the second polymorphic site is PS9. In a preferred embodiment, the disease or condition is selected from the group consisting of atopy, nocturnal asthma, childhood asthma, hypertension, obesity, response to treatment for obesity and MG.

The present invention further provides methods for predicting an asthma patient's response to $\beta$-agonist therapy. In one embodiment, the method comprises determining the genotype for the patient at PS3, PS9 and PS11, wherein the patient is likely to exhibit a good response to a standard dose of the $\beta$-agonist if the patient is homozygous for guanine at each of PS3, PS9 and PS11 or if the patient is heterozygous A/G at each of PS3, PS9 and PS11. If the patient is homozygous A/A/G at PS3, PS9 and PS11, respectively, then the patient is likely to not respond to standard dosages of the $\beta$-agonist. In a preferred embodiment, the $\beta$-agonist is albuterol. Thus, knowledge of a patient's $\beta_2AR$ genotype for PS3, PS9 and PS11 provides a physician with information useful for making determinations as to which drug to administer and dosages of the drug.

BRIEF DESCRIPTION OF THE FIGURES

FIG. 1 illustrates the DNA sequence for a reference sequence of the human $\beta_2AR$ gene (GenBank Accession No. M15169.1; SEQ ID NO:1), with the underlines indicating the start and stop codons, shading indicating the reference coding sequence, and bold nucleotides indicating the polymorphic sites and polymorphisms identified by Applicants in the reference and asthma patient populations.

FIG. 2 illustrates a reference amino acid sequence for $\beta_2AR$ (contiguous lines; SEQ ID NO:2), with the bold amino acids indicating the amino acid variations caused by the polymorphisms at nucleotides 1633, 1666 and 2078 in the $\beta_2AR$ gene.

DESCRIPTION OF THE PREFERRED EMBODIMENTS

Figure 3:
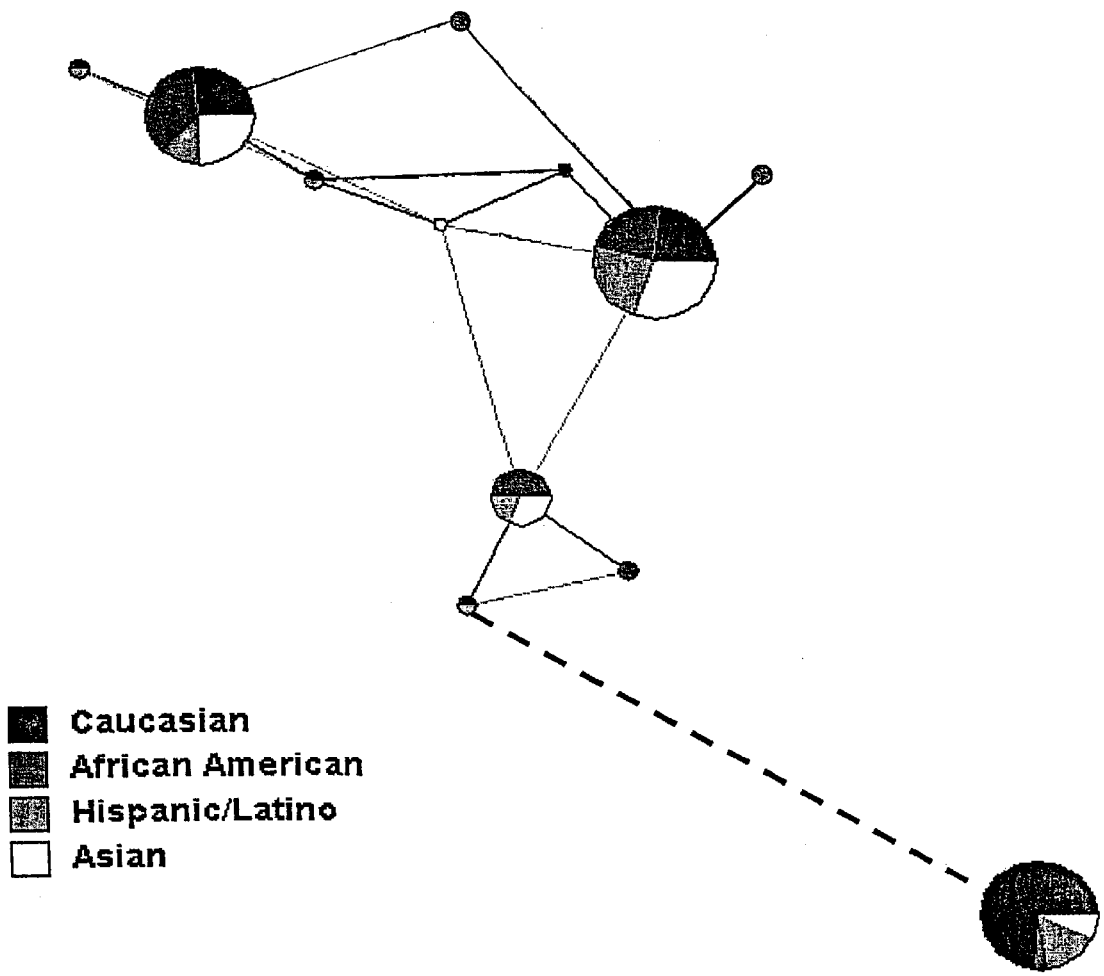
FIG. 3 illustrates the phylogeny of haplotypes of the $\beta_2AR$ gene, with each haplotype represented by a circle, the area of which representing the overall frequency of that haplotype in the reference population, and subdivisions representing the frequency of the haplotype in each of the four population groups. Differences between the haplotypes are indicated by the lines connecting the circles, with solid black lines for single-site differences, gray lines for two-site differences and dashed lines for more than two differences.

In accordance with the present invention, the inventors herein have discovered novel variants of the $\beta_2AR$ gene. As described in more detail below, the inventors herein discovered two novel polymorphic sites by characterizing an approximate 1.8 kb region of the $\beta_2AR$ gene found in genomic DNAs isolated from an asthmatic cohort (121 Caucasians and 13 African Americans) and an Index Repository that contains immortalized cell lines from 93 human individuals, 76 of which comprised a reference population of unrelated individuals self-identified as belonging to one of four major population groups: Caucasian (23 individuals), African descent (19 individuals), Asian (20 individuals) and Hispanic-Latino (15 individuals). In addition, the Index Repository contains three families: two three-generation Caucasian families from the CEPH-Utah cohort and one two-generation African-American family.

Using the $\beta_2AR$ genotypes identified in the Index Repository and patient cohort, in conjunction with the methodology described in the Examples below, the inventors herein also determined the haplotypes found on each chromosome for most individuals in these populations, and determined the frequencies of these haplotypes in the four major population groups. The $\beta_2AR$ genotypes and haplotypes found in the Index Repository and patient cohort include those shown in Table 4 and 5, respectively. It is believed the $\beta_2AR$ polymorphism and haplotype data disclosed herein are useful for studying population diversity, anthropological lineage, the significance of diversity and lineage at the phenotypic level, paternity testing, forensic applications, and for identifying associations between $\beta_2AR$ genetic variation and a trait such as level of drug response or susceptibility to disease.

As disclosed in more detail below, certain pairs of these $\beta_2AR$ haplotypes, designated 2/2, 2/4, 2/6, 4/4 and 4/6 are predictive of bronchodilator response to albuterol. Thus, the present invention is useful in prescribing $\beta$-agonists for treating bronchospasm.

In the context of this disclosure, the following terms shall be defined as follows unless otherwise indicated:

Allele—A particular form of a genetic locus, distinguished from other forms by its particular nucleotide or amino acid sequence.

Gene—A segment of DNA that contains all the information for the regulated biosynthesis of an RNA product, including promoters, exons, introns, and other untranslated regions that control expression.

Genotype—An unphased 5' to 3' sequence of nucleotide pair(s) found at one or more polymorphic sites in a locus on a pair of homologous chromosomes in an individual.

Full-genotype—The unphased 5' to 3' sequence of nucleotide pairs found at all known polymorphic sites in a locus on a pair of homologous chromosomes in a single individual.

Sub-genotype—The unphased 5' to 3' sequence of nucleotides seen at a subset of the known polymorphic sites in a locus on a pair of homologous chromosomes in a single individual.

Genotyping—A process for determining a genotype of an individual.

Haplotype—A phased 5' to 3' sequence of nucleotides found at two or more polymorphic sites in a locus on a single chromosome from a single individual.

Haplotyping—A process for determining a haplotype of an individual.

Haplotype pair—The two haplotypes found for a locus in a single individual.

Full-haplotype—The 5' to 3' sequence of nucleotides found at all known polymorphic sites in a locus on a single chromosome from a single individual.

Sub-haplotype—The 5' to 3' sequence of nucleotides seen at a subset of the known polymorphic sites in a locus on a single chromosome from a single individual.

Haplotype data—Information concerning one or more of the following for a specific gene: a listing of the haplotype pairs in each individual in a population; a listing of the different haplotypes in a population; frequency of each haplotype in that or other populations, and any known associations between one or more haplotypes and a trait.

Isoform—A particular form of a gene, mRNA, cDNA or the protein encoded thereby, distinguished from other forms by its particular sequence and/or structure.

Isogene—One of the isoforms of a gene found in a population. An isogene contains all of the polymorphisms present in the particular isoform of the gene.

Isolated—As applied to a biological molecule such as RNA, DNA, oligonucleotide, or protein, isolated means the molecule is for practical purposes free of other biological molecules such as non-desired nucleic acids, proteins, lipids, carbohydrates, or other material such as cellular debris and growth media. Generally, the term "isolated" is not intended to refer to a complete absence of such material or to absence of water, buffers, or salts, unless they are present in amounts that substantially interfere with the methods of the present invention.

Locus—A location on a chromosome or DNA molecule corresponding to a gene or a physical or phenotypic feature.

Naturally-occurring—A term used to designate that the object it is applied to, e.g., naturally-occurring polynucleotide or polypeptide, can be isolated from a source in nature and which has not been intentionally modified by man.

Nucleotide pair—The nucleotides found at a polymorphic site on corresponding strands of the two copies of a chromosome in an individual.

Phased—As applied to a sequence of nucleotide pairs for two or more polymorphic sites in a locus, phased means the combination of nucleotides present at those polymorphic sites on a single copy of the locus is known.

Polymorphic site (PS)—A position within a locus at which at least two alternative sequences are found in a population.

Polymorphic variant—A gene, mRNA, cDNA, polypeptide or peptide whose nucleotide or amino acid sequence varies from a reference sequence due to the presence of a polymorphism in the gene.

Polymorphism—The sequence variation observed in an individual at a polymorphic site. Polymorphisms include nucleotide substitutions, insertions, deletions and microsatellites and may, but need not, result in detectable differences in gene expression or protein function.

Polymorphism Database—A collection of polymorphism data arranged in a systematic or methodical way and capable of being individually accessed by electronic or other means.

Polynucleotide—A nucleic acid molecule comprised of single-stranded RNA or DNA or comprised of complementary, double-stranded DNA.

Reference Population—A group of subjects or individuals who are predicted to be representative of the genetic variation found in the general population. In preferred embodiments, the reference population represents the genetic variation in the population at a certainty level of at least 85%, preferably at least 90%, more preferably at least 95% and even more preferably at least 99%.

Single Nucleotide Polymorphism (SNP)—Typically, the specific pair of nucleotides observed at a single polymorphic site. In rare cases, three or four nucleotides may be found.

Subject—A human individual whose genotypes or haplotypes or response to treatment or disease state are to be determined.

Treatment—A stimulus administered internally or externally to an individual.

Population Group—A group of individuals sharing a common ethnogeographic origin.

Unphased—As applied to a sequence of nucleotide pairs for two or more polymorphic sites in a locus, unphased means the combination of nucleotides present at those polymorphic sites on a single copy of the locus is not known.

The inventors herein have discovered two novel polymorphic sites in the $\beta_2AR$ gene, which are referred to as of PS2 and PS5 to designate the order in which they are located in the gene (see FIG. 1 and Table 3 below). PS1, PS3, PS4, PS5, PS6, PS7, PS8, PS9, PS10, PS11, PS12, and PS13 designate the previously identified polymorphic sites located at nucleotides 565, 934, 1120, 1221, 1541, 1568, 1633, 1666, 1839, 2078 and 2110 in FIG. 1.

Thus, in one embodiment, the invention provides an isolated polynucleotide comprising a polymorphic variant of the $\beta_2AR$ gene or a fragment of the gene which contains at least one of the novel polymorphic sites described herein. The nucleotide sequence of a variant $\beta_2AR$ gene is identical to the reference genomic sequence for the region of the gene examined, as described in the Examples below, except that it comprises a different nucleotide at one or both of polymorphic sites PS2 and PS5. Similarly, the nucleotide sequence of a variant fragment of the $\beta_2$AR gene is identical to the corresponding portion of the reference sequence except for having a different nucleotide at one or more of these polymorphic sites. Thus, the invention specifically does not include polynucleotides comprising a nucleotide sequence identical to the reference sequence (or other reported $\beta_2$AR sequences) or to portions of the reference sequence (or other reported $\beta_2$AR sequences), except for genotyping oligonucleotides as described below. The location of a polymorphism in a variant gene or fragment is identified by aligning its sequence with SEQ ID NO:1. The polymorphism is selected from the group consisting of cytosine at PS2 and cytosine at PS5. In a preferred embodiment, the polymorphic variant comprises a naturally-occurring isogene of the $\beta_2$AR gene which is defined by any one of haplotypes 1–12 shown in Table 5 below.

Polymorphic variants of the invention may be prepared by isolating a clone containing the $\beta_2$AR gene from a human genomic library. The clone may be sequenced to determine the identity of the nucleotides at the polymorphic sites described herein. Any particular variant claimed herein could be prepared from this clone by performing in vitro mutagenesis using procedures well-known in the art. Alternatively, a polymorphic variant of the $\beta_2$AR gene may be chemically synthesized.

$\beta_2$AR isogenes may be isolated using any method that allows separation of the two "copies" of the $\beta_2$AR gene present in an individual, which, as readily understood by the skilled artisan, may be the same allele or different alleles. Separation methods include targeted in vivo cloning (TIVC) in yeast as described in WO 98/01573, U.S. Pat. No. 5,866,404, and U.S. application Ser. No. 08/987,966. Another method, which is described in U.S. application Ser. No. 08/987,966, uses an allele specific oligonucleotide in combination with primer extension and exonuclease degradation to generate hemizygous DNA targets. Yet other methods are single molecule dilution (SMD) as described in Ruaño et al., Proc. Natl. Acad. Sci. 87:6296–6300, 1990; and allele specific PCR (Ruaño et al., 17 Nucleic Acids. Res. 8392, 1989; Ruaño et al., 19 Nucleic Acids Res. 6877–6882, 1991; Michalatos-Beloin et al., 24 Nucleic Acids Res. 4841–4843, 1996).

The invention also provides $\beta_2$AR genome anthologies, which are collections of $\beta_2$AR isogenes found in a given population. The population may be any group of at least two individuals, including but not limited to a reference population, a population group, a family population, a clinical population, and a same sex population. A $\beta_2$AR genome anthology may comprise individual $\beta_2$AR isogenes stored in separate containers such as microtest tubes, separate wells of a microtitre plate and the like. Alternatively, two or more groups of the $\beta_2$AR isogenes in the anthology may be stored in separate containers. Individual isogenes or groups of isogenes in a genome anthology may be stored in any convenient and stable form, including but not limited to in buffered solutions, as DNA precipitates, freeze-dried preparations and the like. A preferred $\beta_2$AR genome anthology of the invention comprises a set of isogenes defined by the haplotypes shown in Table 5 below.

An isolated polynucleotide containing a polymorphic variant nucleotide sequence of the invention may be operably linked to one or more expression regulatory elements in a recombinant expression vector capable of being propagated and expressing the encoded $\beta_2$AR protein in a prokaryotic or a eukaryotic host cell. Examples of expression regulatory elements which may be used include, but are not limited to, the lac system, operator and promoter regions of phage lambda, yeast promoters, and promoters derived from vaccinia virus, adenovirus, retroviruses, or SV40. Other regulatory elements include, but are not limited to, appropriate leader sequences, termination codons, polyadenylation signals, and other sequences required for the appropriate transcription and subsequent translation of the nucleic acid sequence in a given host cell. Of course, the correct combinations of expression regulatory elements will depend on the host system used. In addition, it is understood that the expression vector contains any additional elements necessary for its transfer to and subsequent replication in the host cell. Examples of such elements include, but are not limited to, origins of replication and selectable markers. Such expression vectors are commercially available or are readily constructed using methods known to those in the art (e.g., F. Ausubel et al., 1987, in "Current Protocols in Molecular Biology", John Wiley and Sons, New York, N.Y.). Host cells which may be used to express the variant $\beta_2$AR sequences of the invention include, but are not limited to, eukaryotic and mammalian cells, such as animal, plant, insect and yeast cells, and prokaryotic cells, such as E. coli, or algal cells as known in the art. The recombinant expression vector may be introduced into the host cell using any method known to those in the art including, but not limited to, microinjection, electroporation, particle bombardment, transduction, and transfection using DEAE-dextran, lipofection, or calcium phosphate (see e.g., Sambrook et al. (1989) in "Molecular Cloning. A Laboratory Manual", Cold Spring Harbor Press, Plainview, N.Y.). In a preferred aspect, eukaryotic expression vectors that function in eukaryotic cells, and preferably mammalian cells, are used. Non-limiting examples of such vectors include vaccinia virus vectors, adenovirus vectors, herpes virus vectors, and baculovirus transfer vectors. Preferred eukaryotic cell lines include COS cells, CHO cells, HeLa cells, NIH/3T3 cells, and embryonic stem cells (Thomson, J. A. et al., 1998 Science 282:1145–1147). Particularly preferred host cells are mammalian cells.

In describing the polymorphic sites identified herein, reference is made to the sense strand of the gene for convenience. However, as recognized by the skilled artisan, nucleic acid molecules containing the $\beta_2$AR gene may be complementary double stranded molecules and thus reference to a particular site on the sense strand refers as well to the corresponding site-on the complementary antisense strand. Thus, reference may be made to the same polymorphic site on either strand and an oligonucleotide may be designed to hybridize specifically to either strand at a target region containing the polymorphic site. Thus, the invention also includes single-stranded polynucleotides which are complementary to the sense strand of the $\beta_2$AR genomic variants described herein.

Polynucleotides comprising a polymorphic gene variant or fragment may be useful for therapeutic purposes. For example, where a patient could benefit from expression, or increased expression, of a particular $\beta_2$AR protein isoform, an expression vector encoding the isoform may be administered to the patient. The patient may be one who lacks the $\beta_2$AR isogene encoding that isoform or may already have at least one copy of that isogene.

In other situations, it may be desirable to decrease or block expression of a particular $\beta_2$AR isogene. Expression of a $\beta_2$AR isogene may be turned off by transforming a targeted organ, tissue or cell population with an expression vector that expresses high levels of untranslatable mRNA for the isogene. Alternatively, oligonucleotides directed against the regulatory regions (e.g., promoter, introns, enhancers, 3' untranslated region) of the isogene may block transcription. Oligonucleotides targeting the transcription initiation site, e.g., between positions −10 and +10 from the start site are preferred. Similarly, inhibition of transcription can be achieved using oligonucleotides that base-pair with region (s) of the isogene DNA to form triplex DNA (see e.g., Gee et al. in Huber, B. E. and B. I. Carr, Molecular and Immunologic Approaches, Futura Publishing Co., Mt. Kisco, N.Y., 1994). Antisense oligonucleotides may also be designed to block translation of $\beta_2$AR mRNA transcribed from a particular isogene. It is also contemplated that ribozymes may be designed that can catalyze the specific cleavage of $\beta_2$AR mRNA transcribed from a particular isogene.

The oligonucleotides may be delivered to a target cell or tissue by expression from a vector introduced into the cell or tissue in vivo or ex vivo. Alternatively, the oligonucleotides may be formulated as a pharmaceutical composition for administration to the patient. Oligoribonucleotides and/or oligodeoxynucleotides intended for use as antisense oligonucleotides may be modified to increase stability and half-life. Possible modifications include, but are not limited to phosphorothioate or 2' O-methyl linkages, and the inclusion of nontraditional bases such as inosine and queosine, as well as acetyl-, methyl-, thio-, and similarly modified forms of adenine, cytosine, guanine, thymine, and uracil which are not as easily recognized by endogenous nucleases.

Effect(s) of the novel polymorphisms and haplotypes identified herein on expression of $\beta_2$AR may be investigated by preparing recombinant cells and/or organisms, preferably recombinant animals, containing a polymorphic variant of the $\beta_2$AR gene. As used herein, "expression" includes but is not limited to one or more of the following: transcription of the gene into precursor mRNA; splicing and other processing of the precursor mRNA to produce mature mRNA; mRNA stability; translation of the mature mRNA into $\beta_2$AR protein (including codon usage and tRNA availability); and glycosylation and/or other modifications of the translation product, if required for proper expression and function.

To prepare a recombinant cell of the invention, the desired $\beta_2$AR isogene may be introduced into the cell in a vector such that the isogene remains extrachromosomal. In such a situation, the gene will be expressed by the cell from the extrachromosomal location. In a preferred embodiment, the $\beta_2$AR isogene is introduced into a cell in such a way that it recombines with the endogenous $\beta_2$AR gene present in the cell. Such recombination requires the occurrence of a double recombination event, thereby resulting in the desired $\beta_2$AR gene polymorphism. Vectors for the introduction of genes both for recombination and for extrachromosomal maintenance are known in the art, and any suitable vector or vector construct may be used in the invention. Methods such as electroporation, particle bombardment, calcium phosphate co-precipitation and viral transduction for introducing DNA into cells are known in the art; therefore, the choice of method may lie with the competence and preference of the skilled practitioner. Examples of cells into which the $\beta_2$AR isogene may be introduced include, but are not limited to, continuous culture cells, such as COS, NIH/3T3, and primary or culture cells of the relevant tissue type, i.e., they are known to express $\beta_2$AR, such as the human embryonic kidney cell line HEK293. Such recombinant cells can be used to compare the biological activities of the different protein variants.

Recombinant organisms, i.e., genetically modified animals, expressing a variant $\beta_2$AR gene are prepared using standard procedures known in the art. Preferably, a construct comprising the variant human gene is introduced into a nonhuman animal or an ancestor of the animal at an embryonic stage, i.e., the one-cell stage, or generally not later than about the eight-cell stage. Genetically-modified animals carrying the constructs of the invention can be made by several methods known to those having skill in the art. One method involves transfecting into the embryo a retrovirus constructed to contain one or more insulator elements, a gene or genes of interest, and other components known to those skilled in the art to provide a complete shuttle vector harboring the insulated gene(s) as a transgene, see e.g., U.S. Pat. No. 5,610,053. Another method involves directly injecting a transgene into the embryo. A third method involves the use of embryonic stem cells. Preferably the genetic modification process results in replacement of the animal's $\beta_2$AR gene with the human $\beta_2$AR gene. Examples of animals into which the human $\beta_2$AR isogenes may be introduced include, but are not limited to, mice, rats, other rodents, and nonhuman primates (see "The Introduction of Foreign Genes into Mice" and the cited references therein, In: Recombinant DNA, Eds. J. D. Watson, M. Gilman, J. Witkowski, and M. Zoller; W.H. Freeman and Company, New York, pages 254–272). Recombinant nonhuman animals stably expressing a human $\beta_2$AR isogene and producing human $\beta_2$AR protein can be used as biological models for studying diseases related to abnormal $\beta_2$AR expression and/or activity, and for screening and assaying various candidate drugs, compounds, and treatment regimens to reduce the symptoms or effects of these diseases.

An additional embodiment of the invention relates to pharmaceutical compositions for treating disorders affected by expression or function of a novel $\beta_2$AR isogene described herein. Such disorders include congestive heart failure, arrhythmia, ischemic heart disease, hypertension, migraine, asthma, chronic obstructive pulmonary disease (COPD), anaphylaxis, obesity, diabetes, myasthenia gravis, and premature labor. The pharmaceutical composition may comprise any of the following active ingredients: a polynucleotide comprising one of these novel $\beta_2$AR isogenes; an antisense oligonucleotide directed against one of the novel $\beta_2$AR isogenes, a polynucleotide encoding such an antisense oligonucleotide, or another compound which activates of inhibits expression of a novel $\beta_2$AR isogene described herein. Preferably, the composition contains the active ingredient in a therapeutically effective amount. By therapeutically effective amount is meant that one or more of the symptoms relating to disorders related to the expression or function of a novel $\beta_2$AR isogene is reduced and/or eliminated. The composition also comprises a pharmaceutically acceptable carrier, examples of which include, but are not limited to, saline, buffered saline, dextrose, and water. Those skilled in the art may employ a formulation most suitable for the active ingredient, whether it is a polynucleotide, oligonucleotide, protein, peptide or small molecule antagonist. The pharmaceutical composition may be administered alone or in combination with at least one other agent, such as a stabilizing compound. Administration of the pharmaceutical composition may be by any number of routes including, but not limited to oral, intravenous, intramuscular, intra-arterial, intramedullary, intrathecal, intraventricular, intradermal, transdermal, subcutaneous, intraperitoneal, intranasal, enteral, topical, sublingual, or rectal. Further details on techniques for formulation and administration may be found in the latest edition of Remington's Pharmaceutical Sciences (Maack Publishing Co., Easton, Pa.).

For any composition, determination of the therapeutically effective dose of active ingredient and/or the appropriate route of administration is well within the capability of those skilled in the art. For example, the dose can be estimated initially either in cell culture assays or in animal models. The animal model may also be used to determine the appropriate concentration range and route of administration. Such information can then be used to determine useful doses and routes for administration in humans. The exact dosage will be determined by the practitioner, in light of factors relating to the patient requiring treatment, including but not limited to severity of the disease state, general health, age, weight and gender of the patient, diet, time and frequency of administration, other drugs being taken by the patient, and tolerance/response to the treatment.

Information on the identity of genotypes and haplotypes for the gene of any particular individual as well as the frequency of such genotypes and haplotypes in any particular population of individuals is expected to be useful for a variety of basic research and clinical applications. Thus, the invention also provides compositions and methods for detecting the novel $\beta_2$AR polymorphisms and haplotypes identified herein.

The compositions comprise at least one $\beta_2$AR genotyping oligonucleotide. In one embodiment, a $\beta_2$AR genotyping oligonucleotide is a probe or primer capable of hybridizing to a target region that is located close to, or that contains, one of the novel polymorphic sites described herein. As used herein, the term "oligonucleotide" refers to a polynucleotide molecule having less than about 100 nucleotides. A preferred oligonucleotide of the invention is 10 to 35 nucleotides long. More preferably, the oligonucleotide is between 15 and 30, and most preferably, between 20 and 25 nucleotides in length. The oligonucleotide may be comprised of any phosphorylation state of ribonucleotides, deoxyribonucleotides, and acyclic nucleotide derivatives, and other functionally equivalent derivatives. Alternatively, oligonucleotides may have a phosphate-free backbone, which may be comprised of linkages such as carboxymethyl, acetamidate, carbamate, polyamide (peptide nucleic acid (PNA)) and the like (Varma, R. in Molecular Biology and Biotechnology, A Comprehensive Desk Reference, Ed. R. Meyers, VCH Publishers, Inc. (1995), pages 617–620). Oligonucleotides of the invention may be prepared by chemical synthesis using any suitable methodology known in the art, or may be derived from a biological sample, for example, by restriction digestion. The oligonucleotides may be labeled, according to any technique known in the art, including use of radiolabels, fluorescent labels, enzymatic labels, proteins, haptens, antibodies, sequence tags and the like.

Genotyping oligonucleotides of the invention must be capable of specifically hybridizing to a target region of a $\beta_2$AR polynucleotide, i.e., a $\beta_2$AR isogene. As used herein, specific hybridization means the oligonucleotide forms an anti-parallel double-stranded structure with the target region under certain hybridizing conditions, while failing to form such a structure when incubated with a non-target region or a non-$\beta_2$AR polynucleotide under the same hybridizing conditions. Preferably, the oligonucleotide specifically hybridizes to the target region under conventional high stringency conditions. The skilled artisan can readily design and test oligonucleotide probes and primers suitable for detecting polymorphisms in the $\beta_2$AR gene using the polymorphism information provided herein in conjunction with the known sequence information for the $\beta_2$AR gene and routine techniques.

A nucleic acid molecule such as an oligonucleotide or polynucleotide is said to be a "perfect" or "complete" complement of another nucleic acid molecule if every nucleotide of one of the molecules is complementary to the nucleotide at the corresponding position of the other molecule. A nucleic acid molecule is "substantially complementary" to another molecule if it hybridizes to that molecule with sufficient stability to remain in a duplex form under conventional low-stringency conditions. Conventional hybridization conditions are described, for example, by Sambrook J. et al., in Molecular Cloning, A Laboratory Manual, $2^{nd}$ Edition, Cold Spring Harbor Press, Cold Spring Harbor, N.Y. (1989) and by Haymes, B. D. et al. in Nucleic Acid Hybridization, A Practical Approach, IRL Press, Washington, D.C. (1985). While perfectly complementary oligonucleotides are preferred for detecting polymorphisms, departures from complete complementarity are contemplated where such departures do not prevent the molecule from specifically hybridizing to the target region. For example, an oligonucleotide primer may have a non-complementary fragment at its 5' end, with the remainder of the primer being complementary to the target region. Alternatively, non-complementary nucleotides may be interspersed into the oligonucleotide probe or primer as long as the resulting probe or primer is still capable of specifically hybridizing to the target region.

Preferred genotyping oligonucleotides of the invention are allele-specific oligonucleotides. As used herein, the term allele-specific oligonucleotide (ASO) means an oligonucleotide that is able, under sufficiently stringent conditions, to hybridize specifically to one allele of a gene, or other locus, at a target region containing a polymorphic site while not hybridizing to the corresponding region in another allele(s). As understood by the skilled artisan, allele-specificity will depend upon a variety of readily optimized stringency conditions, including salt and formamide concentrations, as well as temperatures for both the hybridization and washing steps. Examples of hybridization and washing conditions typically used for ASO probes are found in Kogan et al., "Genetic Prediction of Hemophilia A" in PCR Protocols, A Guide to Methods and Applications, Academic Press, 1990 and Ruano et al., 87 Proc. Natl. Acad. Sci. USA 6296–6300, 1990. Typically, an allele-specific oligonucleotide will be perfectly complementary to one allele while containing a single mismatch for another allele.

Allele-specific oligonucleotide probes which usually provide good discrimination between different alleles are those in which a central position of the oligonucleotide probe aligns with the polymorphic site in the target region (e.g., approximately the $7^{th}$ or $8^{th}$ position in a 15 mer, the $8^{th}$ or $9^{th}$ position in a 16 mer, the $10^{th}$ or $11^{th}$ position in a 20 mer). A preferred ASO pr detecting $\beta_2$AR gene polymorphisms at PS2 and PS5 comprises a nucleotide sequence selected from the group consisting of:

5'-TGCATGTCGGTGAGC-3' (SEQ ED NO:3) and its complement;

5'-TGCATGTAGGTGAGC-3' (SEQ ID NO:4) and its complement;

5'-GGTGGCCCGCCCTCC-3' (SEQ ID NO:5) and its complement;

and

5'-GGTGGCCTGCCCTCC-3' (SEQ ID NO:6) and its complement.

An allele-specific oligonucleotide primer of the invention has a 3' terminal nucleotide, or preferably a 3' penultimate nucleotide, that is complementary to only one nucleotide of a particular SNP, thereby acting as a primer for polymerase-mediated extension only if the allele containing that nucleotide is present. Allele-specific oligonucleotide primers hybridizing to either the coding or noncoding strand are contemplated by the invention. A preferred ASO forward primer for detecting $\beta_2AR$ gene polymorphisms at PS2 and PS5 comprises a nucleotide sequence selected from the group consisting of:

CGAGTGTGCATGTCG (SEQ ID NO:7);

CTCCCAGCTCACCGA (SEQ ID NO:8);

CGAGTGTGCATGTAG (SEQ ID NO:9);

CTCCCAGCTCACCTA (SEQ ID NO:10);

AGCAGTGGTGGCCCG (SEQ ID NO:11);

CTCCCTGGAGGGCGG (SEQ ID NO:12);

AGCAGTGGTGGCCTG (SEQ ID NO:13)

and

CTCCCTGGAGGGCAG (SEQ ID NO:14).

Other genotyping oligonucleotides of the invention hybridize to a target region located one to several nucleotides downstream of one of the novel polymorphic sites identified herein. Such oligonucleotides are useful in polymerase-mediated primer extension methods for detecting $\beta_2AR$ gene polymorphisms and thus are referred to herein as "primer-extension oligonucleotides". In a preferred embodiment, the 3'-terminus of a primer-extension oligonucleotide is a deoxynucleotide complementary to the nucleotide located immediately adjacent to the polymorphic site. A particularly preferred oligonucleotide primer for detecting $\beta_2AR$ gene polymorphisms at PS2 and PS5 by primer extension terminates in a nucleotide sequence selected from the group consisting of:

GTGTGCATGT (SEQ ID NO:15);

CCAGCTCACC (SEQ ID NO:16);

AGTGGTGGCC (SEQ ID NO:17);

and

CCTGGAGGGC (SEQ ID NO:18).

In some embodiments, a composition contains two or more differently labeled genotyping oligonucleotides for simultaneously probing the identity of nucleotides at two or more polymorphic sites. It is also contemplated that primer compositions may contain two or more sets of allele-specific primer pairs to allow simultaneous targeting and amplification of two or more regions containing a polymorphic site.

As further described below, the inventors herein have discovered that a patient's bronchodilating response to albuterol may be predicted with high confidence by genotyping only three of the polymorphic sites in the $\beta_2AR$ gene: PS3, PS9 and PS11. Thus, the invention also provides a diagnostic kit for predicting an individual's response to a $\beta$-agonist. In one embodiment, the kit comprises a set of genotyping oligonucleotides for genotyping PS3, PS9 and PS11 in the $\beta_2AR$ gene packaged in a container. The kit may also contain other components such as hybridization buffer, where the oligonucleotides are to be used as allele-specific probes, or dideoxynucleotide triphosphates (ddNTPs), where the polymorphic sites are to be detected by primer extension. In a preferred embodiment, the set of genotyping oligonucleotides consists of three primer extension oligonucleotides, one for genotyping PS3, one for genotyping PS9 and one for genotyping PS11. The kit may also contain a polymerase and a reaction buffer optimized for primer extension mediated by the polymerase. Preferred kits may also include detection reagents, such as biotin- or fluorescent-tagged oligonucleotides or ddNTPs and/or an enzyme-labeled antibody and one or more substrates that generate a detectable signal when acted on by the enzyme. In a preferred embodiment, each of the genotyping oligonucleotides and all other reagents in the kit have been quality tested for optimal performance in a genotyping assay for each of PS3, PS9 and PS11 and the kit also contains instructions for performing the assay and assigning a $\beta_2AR$ haplotype pair from the results. It will be understood by the skilled artisan that the set of genotyping oligonucleotides and reagents for performing the genotyping assay will be provided in separate receptacles placed in the container if appropriate to preserve biological or chemical activity and enable proper use in the assay.

$\beta_2AR$ genotyping oligonucleotides of the invention may also be immobilized on or synthesized on a solid surface such as a microchip, bead, or glass slide (see, e.g., WO 98/20020 and WO 98/20019). Such immobilized genotyping oligonucleotides may be used in a variety of polymorphism detection assays, including but not limited to probe hybridization and polymerase extension assays. Immobilized $\beta_2AR$ genotyping oligonucleotides of the invention may comprise an ordered array of oligonucleotides designed to rapidly screen a DNA sample for polymorphisms in multiple genes at the same time.

The above described oligonucleotide compositions and kits are useful in methods for genotyping and/or haplotyping the $\beta_2AR$ gene in an individual. As used herein, the terms "$\beta_2AR$ genotype" and "$\beta_2AR$ haplotype" mean the genotype or haplotype contains the nucleotide pair or nucleotide, respectively, that is present at one or both of PS2 and PS5 and may optionally also include the nucleotide pair or nucleotide present at one or more additional polymorphic sites in the $\beta_2AR$ gene. The additional polymorphic sites may be currently known polymorphic sites or sites that are subsequently discovered. In preferred embodiments, the additional polymorphic sites are selected from the group consisting of PS1, PS3, PS4, PS6, PS7, PS8, PS9, PS10, PS11, PS12 and PS13.

One embodiment of the genotyping method involves isolating from the individual a nucleic acid mixture comprising the two copies of the $\beta_2AR$ gene, or a fragment thereof, that are present in the individual, and determining the identity of the nucleotide pair at one or more of PS2 and PS5 in the two copies to assign a $\beta_2AR$ genotype to the individual. As will be readily understood by the skilled artisan, the two "copies" of a gene in an individual may be the same allele or may be different alleles. In a particularly preferred embodiment, the genotyping method comprises determining the identity of the nucleotide pair at each of PS1, PS2, PS3, PS4, PS5, PS6, PS7, PS8, PS9, PS10, PS11, PS12, and PS13.

Typically, the nucleic acid mixture is isolated from a biological sample taken from the individual, such as a blood sample or tissue sample. Suitable tissue samples include whole blood, semen saliva, tears, urine, fecal material, sweat, buccal, skin and hair. The nucleic acid mixture may be comprised of genomic DNA, mRNA, or cDNA and, in the latter two cases, the biological sample must be obtained from an organ in which the β₂AR gene is expressed. Furthermore it will be understood by the skilled artisan that mRNA or cDNA preparations would not be used to detect polymorphisms located in introns or in 5' and 3' nontranscribed regions. If a β₂AR gene fragment is isolated, it must contain the polymorphic site(s) to be genotyped.

One embodiment of the haplotyping method comprises isolating from the individual a nucleic acid molecule containing only one of the two copies of the β₂AR gene, or a fragment thereof, that is present in the individual and determining in that copy the identity of the nucleotide at one or both of polymorphic sites PS2 and PS5 in that copy to assign a β₂AR haplotype to the individual. The nucleic acid may be isolated using any method capable of separating the two copies of the β₂AR gene or fragment such as one of the methods described above for preparing β₂AR isogenes, with targeted in vivo cloning being the preferred approach. As will be readily appreciated by those skilled in the art, any individual clone will only provide haplotype information on one of the two β₂AR gene copies present in an individual. If haplotype information is desired for the individual's other copy, additional β₂AR clones will need to be examined. Typically, at least five clones should be examined to have more than a 90% probability of haplotyping both copies of the β₂AR gene in an individual. In a particularly preferred embodiment, the nucleotide at each of PS1, PS2, PS3, PS4, PS5, PS6, PS7, PS8, PS9, PS10, PS11, PS12 and PS13 is identified.

In a preferred embodiment, a β₂AR haplotype pair is determined for an individual by identifying the phased sequence of nucleotides at one or both of PS2 and PS5 in each copy of the β₂AR that is gene present in the individual. In a particularly preferred embodiment, the haplotyping method comprises identifying the phased sequence of nucleotides at each of PS1, PS2, PS3, PS4, PS5, PS6, PS7, PS8, PS9, PS10, PS11, PS12 and PS13 in each copy of the β₂AR gene. When haplotyping both copies of the gene, the identifying step is preferably performed with each copy of the gene being placed in separate containers. However, it is also envisioned that if the two copies are labeled with different tags, or are otherwise separately distinguishable or identifiable, it could be possible in some cases to perform the method in the same container. For example, if first and second copies of the gene are labeled with different first and second fluorescent dyes, respectively, and an genotyping oligonucleotide labeled with yet a third different fluorescent dye is used to assay the polymorphic site(s), then detecting a combination of the first and third dyes would identify the polymorphism in the first gene copy while detecting a combination of the second and third dyes would identify the polymorphism in the second gene copy.

Another aspect of the invention is a method for predicting an individual's bronchodilating response to a β-agonist, which comprises assigning a β₂AR haplotype pair to the individual and using the assigned haplotype pair to make a response prediction selected from the group consisting of: assignment of β₂AR haplotype pair 4/6 or 2/2 predicts a good bronchodilating response; assignment of β₂AR haplotype pair 2/6 predicts an intermediate bronchodilating response and assignment of β₂AR haplotype pair 2/4 or 4/4 predicts no bronchodilating response. These haploytpes pairs are set forth in Table 6. In a preferred embodiment, the β-agonist is albuterol.

In one embodiment, the assigning step comprises determining a genotype for PS3, PS9 and PS11 in the individual's β₂AR gene and using the genotype to assign the haplotype pair. The genotype and haplotype pair combinations that are predictive of response to β-agonists are shown in Table 1 below.

TABLE 1

| Haplotype pairs predicted from genotypes. | |
|---|---|
| Genotype for PS3, PS9 and PS11 | Haplotype Pair |
| G/G, G/G, G/G | 2/2 |
| A/A, A/A, A/A | 4/4 |
| A/G, A/G, A/G | 4/6 |
| G/G, G/G, G/A | 2/6 |
| A/G, A/G, G/G | 2/4 |

Additional genotype and haplotype pair combinations that exist in the population are shown in Table 4 below. The ability to assign the β₂AR haplotype pair by genotyping only PS3, PS9 and PS11 is based on linkage disequilibrium between certain groups of polymorphic sites in the β₂AR gene (FIG. 4) as well as the frequencies of the individual β₂AR haplotypes in the different population groups (Table 5). Thus, where an individual is heterozygous at two or all three of PS3, PS9 and PS11, e.g., more than one possible haplotype pair is consistent with the individual's genotype for PS3, PS9 and PS11, the probability of assigning the haplotype pair correctly is readily calculated from the frequencies that the individual haplotypes occur in that individual's population group. Based on the sample size in the study described below, it is believed that an individual's haplotype pair would be accurately predicted greater than 90% of the time. In a preferred embodiment, an individual's β₂AR haplotype pair is assigned by genotyping one or more additional polymorphic sites selected from the group consisting of PS1, PS2, PS4, PS5, PS6, PS7, PS8, PS9, PS10, PS12 and PS13.

The ability to predict a patient's response to a β-agonist is useful for physicians in making decisions about how to treat an asthma patient for bronchospasm. An asthma patient whose haplotype pair indicates the patient will probably respond well to the agonist would be a better candidate for β-agonist therapy than a patient who is likely to exhibit an intermediate response or no response, and the physician would be able to determine with less trial and error which individuals should receive an alternative form of therapy.

The following pairs of β₂AR sites exhibit about 100% linkage disequilibrium in Caucasians: PS1 and PS10 (amino acid 27); PS3 and PS9 (amino acid 16); PS4 and PS10; and PS6 and PS10. This provides the basis for another aspect of the invention, which is a method for predicting a Caucasian individual's genotype for one or both of PS9 and PS10, both of which have been linked to various diseases and conditions. The method comprises determining a first genotype for one or more of PS1, PS3, PS4 or PS6 in the individual's β₂AR gene and using the first genotype to assign a second genotype for one or both of PS9 and PS10 to the individual. Preferably, the first and second genotypes correspond to one of the genotype combinations shown in Table 2 below:

TABLE 2

| Genotype Combinations | |
|---|---|
| Polymorphic Sites | Genotypes |
| PS1, PS10 | A/A, G/G |
| PS1, PS10 | G/G, C/C |
| PS1, PS10 | A/G, G/C |
| PS3, PS9 | A/A, A/A |

TABLE 2-continued

Genotype Combinations

| Polymorphic Sites | Genotypes |
|---|---|
| PS3, PS9 | G/G, G/G |
| PS3, PS9 | A/G, A/G |
| PS4, PS10 | C/C, C/C |
| PS4, PS10 | G/G, G/G |
| PS4, PS10 | C/G, C/G |
| PS6, PS10 | C/C, G/G |
| PS6, PS10 | T/T, C/C |
| PS6, PS10 | C/T, G/C |
| PS1, PS3, PS9, PS10 | G/G, A/A, A/A, C/C |
| PS1, PS3, PS9, PS10 | A/G, G/G, G/G, G/C |
| PS1, PS3, PS9, PS10 | A/A, G/G, G/G, G/G |
| PS1, PS3, PS9, PS10 | G/G, A/G, A/G, C/C |
| PS1, PS3, PS9, PS10 | A/G, A/G, A/G, G/C |
| PS3, PS4, PS9, PS10 | A/A, C/C, A/A, C/C |
| PS3, PS4, PS9, PS10 | G/G, G/G, G/G, G/G |
| PS3, PS4, PS9, PS10 | A/G, C/C, A/G, C/C |
| PS3, PS6, PS9, PS10 | A/A, T/T, A/A, C/C |
| PS3, PS6, PS9, PS10 | G/G, C/C, G/G, G/G |
| PS3, PS6, PS9, PS10 | A/G, T/T, A/G, C/C |
| PS3, PS6, PS9, PS10 | G/G, C/T, G/G, G/C |
| PS3, PS6, PS9, PS10 | A/G, C/T, A/G, G/C |

In a preferred embodiment, the first genotype is for PS3 and one or more of PS1, PS4 and PS6, and the second genotype is for both PS9 and PS10.

This genotyping prediction method is useful for predicting the individual's predisposition to a disease or condition associated with one of the alternative alleles at PS9 or PS10 in the $\beta_2AR$ gene. For example, a PS9 genotype of G/G means the individual expresses only the $\beta_2AR$ Gly16 variant and is predisposed to atopy and nocturnal asthma, whereas a PS9 genotype of A/A indicates the individual expresses only the $\beta_2AR$ Arg 16 variant and is predisposed to MG. Similarly, a PS10 genotype of C/C means the individual expresses only the $\beta_2AR$ Gln27 variant and is predisposed to childhood asthma, while a PS10 genotype means the individual expresses only the $\beta_2AR$ Glu27 variant and is predisposed to obesity. Where the first genotype is for PS3 and one or more of PS1, PS4, and PS6, the genotypes at PS9 and PS10 can be predicted, and such genotypes are useful for predicting severity of asthma (G/G at PS9, G/G at PS10) and BHR. However, the present invention is not limited to the $\beta_2AR$ polymorphism or haplotype associations presently known but is applicable to future discoveries of associations between polymorphisms or haplotype for PS9 and PS10 and disease, severity of disease, staging of disease, or any other phenotype.

It is also contemplated that the above genotyping and haplotyping methods of the invention may be performed in combination with identifying the genotype(s) and/or haplotype(s) for other genomic regions.

In the genotyping and haplotyping methods of the invention, the identity of a nucleotide (or nucleotide pair) at a polymorphic site may be determined by amplifying a target region(s) containing the polymorphic site(s) directly from one or both copies of the $\beta_2AR$ gene present in the individual and the sequence of the amplified region(s) determined by conventional methods. It will be readily appreciated by the skilled artisan that only one nucleotide will be detected at a polymorphic site in individuals who are homozygous at that site, while two different nucleotides will be detected if the individual is heterozygous for that site. The polymorphism may be identified directly, known as positive-type identification, or by inference, referred to as negative-type identification. For example, where a SNP is known to be guanine and cytosine in a reference population, a site may be positively determined to be either guanine or cytosine for an individual homozygous at that site, or both guanine and cytosine, if the individual is heterozygous at that site. Alternatively, the site may be negatively determined to be not guanine (and thus cytosine/cytosine) or not cytosine (and thus guanine/guanine).

The target region(s) may be amplified using any oligonucleotide-directed amplification method, including but not limited to polymerase chain reaction (PCR) (U.S. Pat. No. 4,965,188), ligase chain reaction (LCR) (Barany et al., *Proc. Natl. Acad. Sci. USA* 88:189–193, 1991; WO90/01069), and oligonucleotide ligation assay (OLA) (Landegren et al., *Science* 241:1077–1080, 1988). Oligonucleotides useful as primers or probes in such methods should specifically hybridize to a region of the nucleic acid that contains or is adjacent to the polymorphic site. Typically, the oligonucleotides are between 10 and 35 nucleotides in length and preferably, between 15 and 30 nucleotides in length. Most preferably, the oligonucleotides are 20 to 25 nucleotides long. The exact length of the oligonucleotide will depend on many factors that are routinely considered and practiced by the skilled artisan.

Other known nucleic acid amplification procedures may be used to amplify the target region including transcription-based amplification systems (U.S. Pat. No. 5,130,238; EP 329,822; U.S. Pat. No. 5,169,766, WO89/06700) and iso-thermal methods (Walker et L., *Proc. Natl. Acad. Sci. USA* 89:392–396, 1992.

A polymorphism in the target region may also be assayed before or after amplification using one of several hybridization-based methods known in the art. Typically, allele-specific oligonucleotides are utilized in performing such methods. The allele-specific oligonucleotides may be used as differently labeled probe pairs, with one member of the pair showing a perfect match to one variant of a target sequence and the other member showing a perfect match to a different variant. In some embodiments, more than one polymorphic site may be detected at once using a set of allele-specific oligonucleotides or oligonucleotide pairs. Preferably, the members of the set have melting temperatures within 5° C., and more preferably within 2° C., of each other when hybridizing to each of the polymorphic sites being detected.

Hybridization of an allele-specific oligonucleotide to a target polynucleotide may be performed with both entities in solution, or such hybridization may be performed when either the oligonucleotide or the target polynucleotide is covalently or noncovalently affixed to a solid support. Attachment may be mediated, for example, by antibody-antigen interactions, poly-L-Lys, streptavidin or avidin-biotin, salt bridges, hydrophobic interactions, chemical linkages, UV cross-linking baking, etc. Allele-specific oligonucleotides may be synthesized directly on the solid support or attached to the solid support subsequent to synthesis. Solid-supports suitable for use in detection methods of the invention include substrates made of silicon, glass, plastic, paper and the like, which may be formed, for example, into wells (as in 96-well plates), slides, sheets, membranes, fibers, chips, dishes, and beads. The solid support may be treated, coated or derivatized to facilitate the immobilization of the allele-specific oligonucleotide or target nucleic acid.

The genotype or haplotype for one or more polymorphic sites in the $\beta_2AR$ gene of an individual may also be determined by hybridization of one or both copies of the gene, or a fragment thereof, to nucleic acid arrays and subarrays such as described in WO 95/11995. The arrays would contain a battery of allele-specific oligonucleotides representing each of the polymorphic sites to be included in the genotype or haplotype.

The identity of polymorphisms may also be determined using a mismatch detection technique, including but not limited to the RNase protection method using riboprobes (Winter et al., *Proc. Natl. Acad. Sci. USA* 82:7575, 1985; Meyers et al., *Science* 230:1242, 1985) and proteins which recognize nucleotide mismatches, such as the *E. coli* mutS protein (Modrich, P. *Ann. Rev. Genet.* 25:229–253 (1991). Alternatively, variant alleles can be identified by single strand conformation polymorphism (SSCP) analysis (Orita et al., *Genomics* 5:874–879, 1989; Humphries et al., in *Molecular Diagnosis of Genetic Diseases,* R. Elles, ed., pp 321–340, 1996) or denaturing gradient gel electrophoresis (DGGE) (Wartell et al., *Nucl. Acids Res.* 18:2699–2706, 1990; Sheffield et al., *Proc. Natl. Acad. Sci. USA* 86:232–236, 1989).

A polymerase-mediated primer extension method may also be used to identify the polymorphism(s). Several such methods have been described in the patent and scientific literature and include the "Genetic Bit Analysis" method (WO92/15712) and the ligase/polymerase mediated genetic bit analysis (U.S. Pat. No. 5,679,524. Related methods are disclosed in WO91/02087, WO90/09455, WO95/17676, and U.S. Pat. Nos. 5,302,509 and 5,945,283. Extended primers containing a polymorphism may be detected by mass spectrometry as described in U.S. Pat. No. 5,605,798. An other primer extension method is allele-specific PCR (Ruano et al., *Nucl. Acids Res.* 17:8392, 1989; Ruano et al., *Nucl. Acids Res.* 19, 6877–6882, 1991; WO 93/22456; Turki et al., *J. Clin. Invest.* 95:1635–1641, 1995). In addition, multiple polymorphic sites may be investigated by simultaneously amplifying multiple regions of the nucleic acid using sets of allele-specific primers as described in Wallace et al. (WO89/10414).

The above described genotyping methods are useful in methods for determining the frequency of a $\beta_2AR$ genotype or haplotype in a population. The method comprises determining the genotype or the haplotype pair for the $\beta_2AR$ gene that is present in each member of the population and calculating the frequency any particular $\beta_2AR$ genotype or haplotype is found in the population. In a preferred embodiment, the $\beta_2AR$ genotype comprises the nucleotide pair(s) detected at each of PS1–PS13. The population may be a reference population, a family population, a same sex population, a population group, a trait population (e.g., a group of individuals exhibiting a trait of interest such as a medical condition or response to a therapeutic treatment).

Frequency data for such $\beta_2AR$ genotypes or haplotypes in reference and trait populations are useful for identifying an association between a trait and any novel $\beta_2AR$ polymorphism, genotype or haplotype. The trait may be any detectable phenotype, including but not limited to susceptibility to a disease or response to a treatment. The method involves obtaining data on the frequency of the genotype(s) or haplotype(s) of interest in a reference population as well as in a population exhibiting the trait. Frequency data for one or both of the reference and trait populations may be obtained by genotyping or haplotyping the $\beta_2AR$ gene in each individual in the populations using one of the methods described above. The haplotypes for the trait population may be determined directly or, alternatively, by the predictive genotype to haplotype approach described above. In another embodiment, the frequency data for the reference and/or trait populations is obtained by accessing previously determined frequency data, which may be in written or electronic form. For example, the frequency data may be present in a database that is accessible by a computer. Once the frequency data is obtained, the frequencies of the genotype(s) or haplotype(s) of interest in the reference and trait populations are compared. In a preferred embodiment, the frequencies of all genotypes and/or haplotypes observed in the populations are compared. If a particular genotype or haplotype for the $\beta_2AR$ gene is more frequent in the trait population than in the reference population at a statistically significant amount, then the trait is predicted to be associated with that $\beta_2AR$ genotype or haplotype. Preferably, the $\beta_2AR$ genotype or haplotype being compared in the trait and reference populations is selected from the fall-genotypes and full-haplotypes shown in Tables 4 and 5 respectively, or from sub-genotypes and sub-haplotypes derived from these genotypes and haplotypes.

In a preferred embodiment of the method, the trait of interest is a clinical response exhibited by a patient to some therapeutic treatment, for example, response to a drug targeting $\beta_2AR$ or response to a therapeutic treatment for a medical condition. As used herein, "medical condition" includes but is not limited to any condition or disease manifested as one or more physical and/or psychological symptoms for which treatment is desirable, and includes previously and newly identified diseases and other disorders. As used herein the term "clinical response" means any or all of the following: a quantitative measure of the efficacy of the therapy, no efficacy, and adverse events (i.e., side effects).

In order to deduce a correlation between clinical response to a treatment and a $\beta_2AR$ genotype or haplotype, it is necessary to obtain data on the clinical responses exhibited by a population of individuals who received the treatment, hereinafter the "clinical population". This clinical data may be obtained by analyzing the results of a clinical trial that has already been run and/or the clinical data may be obtained by designing and carrying out one or more new clinical trials. As used herein, the term "clinical trial" means any research study designed to collect clinical data on responses to a particular treatment, and includes but is not limited to phase I, phase II and phase III clinical trials. Standard methods are used to define the patient population and to enroll subjects.

It is preferred that selection of individuals for the clinical population comprises grading such candidate individuals for the existence of the medical condition of interest and then including or excluding individuals based upon the results of this assessment. This is important in cases where the symptom(s) being presented by the patients can be caused by more than one underlying condition, and where treatment of the underlying conditions are not the same. An example of this would be where patients experience breathing difficulties that are due to either asthma or respiratory infections. If both sets were treated with an asthma medication, there would be a spurious group of apparent non-responders that did not actually have asthma. These people would affect the ability to detect any correlation between haplotype and treatment outcome. This grading of potential patients could employ a standard physical exam or one or more lab tests. Alternatively, grading of patients could use haplotyping for situations where there is a strong correlation between haplotype pair and disease susceptibility or severity.

The therapeutic treatment of interest, or the control treatment (active agent or placebo in controlled trials), is administered to each individual in the trial population and each individual's response to the treatment is measured using one or more predetermined criteria. It is contemplated that in many cases, the trial population will exhibit a range of responses and that the investigator will choose the number of responder groups (e.g., low, medium, high) made up by the various responses. In addition, the β₂AR gene for each individual in the trial population is genotyped and/or haplotyped, which may be done before or after administering the treatment.

After both the clinical and polymorphism data have been obtained, correlations between individual response and β₂AR genotype or haplotype content are created. Correlations may be produced in several ways. In one method, individuals are grouped by their β₂AR genotype or haplotype (or haplotype pair) (also referred to as a polymorphism group), and then the averages and standard deviations of continuous clinical responses exhibited by the members of each polymorphism group are calculated.

These results are then analyzed to determine if any observed variation in clinical response between polymorphism groups is statistically significant. Statistical analysis methods which may be used are described in L. D. Fisher and G. vanBelle, "Biostatistics: A Methodology for the Health Sciences", Wiley-Interscience (New York) 1993. This analysis may also include a regression calculation of which polymorphic sites in the β₂AR gene give the most significant contribution to the differences in phenotype. One regression model useful in the invention starts with a model of the form $$r = r_0 + S \times d$$

where r is the response, $r_0$ is a constant called the "intercept", S is the slope and d is the dose.

To determine the dose, the most-common and least common nucleotides at the polymorphic site are first defined. Then, for each individual in the trial population, one calculates a "dose" as the number of least-common nucleotides the individual has at the polymorphic site of interest. This value can be 0 (homozygous for the least-common nucleotide), 1 (heterozygous), or 2 (homozygous for the most common nucleotide). An individual's "response" is the value of the clinical measurement. Standard linear regression methods are then used to fit all the individuals' doses and responses to a single model (see e.g., L. D. Fisher and G. vanBelle, supra, Ch 9). The outputs of the regression calculation are the intercept $r_0$, the slope S, and the variance (which measures how well the data fits this simple linear model). The Students t-test value and the level of significance can then be calculated for each of the polymorphic sites.

A second method for finding correlations between β₂AR haplotype content and clinical responses uses predictive models based on error-minimizing optimization algorithms. One of many possible optimization algorithms is a genetic algorithm (R. Judson, "Genetic Algorithms and Their Uses in Chemistry" in Reviews in Computational Chemistry, Vol. 10, pp. 1–73, K. B. Lipkowitz and D. B. Boyd, eds. (VCH Publishers, New York, 1997). Simulated annealing (Press et al., "Numerical Recipes in C: The Art of Scientific Computing", Cambridge University Press (Cambridge) 1992, Ch. 10), neural networks (E. Rich and K. Knight, "Artificial Intelligence", 2$^{nd}$ Edition McGraw-Hill; New York, 1991, Ch. 18), standard gradient descent methods (Press et al., supra Ch. 10), or other global or local optimization approaches (see discussion in Judson, supra) could also be used. As an example, a genetic algorithm approach is described herein. This method searches for optimal parameters or weights in linear or non-linear models connecting β₂AR haplotype loci and clinical outcome. One model is of the form $$C = C_0 + \sum_{\alpha} \left( \sum_i w_{i,\alpha} R_{i,\alpha} + \sum_i w'_{i,\alpha} L_{i,\alpha} \right) \quad [1]$$

where C is the measured clinical outcome, i goes over all polymorphic sites, α over all candidate genes, $C_0$, $w_{i,\alpha}$ and $w'_{i,\alpha}$ are variable weight values, $R_{i,\alpha}$ is equal to 1 if site i in gene α in the first haplotype takes on the most common nucleotide and: −1 if it takes on the less common nucleotide. $L_{i,\alpha}$ is the same as $R_{i,\alpha}$ except for the second haplotype. The constant term $C_0$ and the weights $w_{i,\alpha}$ and $w'_{i,\alpha}$ are varied by the genetic algorithm during a search process that minimizes the error between the measured value of C and the value calculated from Equation 1. Models other than the one given in Equation 1 can be readily incorporated by those skilled in the art for analyzing the clinical and polymorphism data. The genetic algorithm is especially suited for searching not only over the space of weights in a particular model but also over the space of possible models (Judson, supra).

Correlations may also be analyzed using analysis of variation (ANOVA) techniques to determine how much of the variation in the clinical data is explained by different subsets of the polymorphic sites in the β₂AR gene. ANOVA is used to test hypotheses about whether a response variable is caused by or correlated with one or more traits or variables (in this case, polymorphism groups) that can be measured (Fisher and vanBelle, supra, Ch. 10). These traits or variables are called the independent variables. To carry out ANOVA, the independent variable(s) are measured and individuals are placed into groups based on their values for these variables. In this case, the independent variable(s) refers to the combination of polymorphisms present at a subset of the polymorphic sites, and thus, each group contains those individuals with a given genotype or haplotype pair. The variation in response within the groups and also the variation between groups is then measured. If the within-group response variation is large (people in a group have a wide range of responses) and the response variation between groups is small (the average responses for all groups are about the same) then it can be concluded that the independent variables used for the grouping are not causing or correlated with the response variable. For instance, if people are grouped by month of birth (which should have nothing to do with their response to a drug) the ANOVA calculation should show a low level of significance. However, if the response variation is larger between groups than within groups, the F-ratio (="between groups" divided by "within groups") is greater than one. Large values of the F-ratio indicate that the independent variable is causing or correlated with the response. The calculated F-ratio is preferably compared with the critical F-distribution value at whatever level of significance is of interest. If the F-ratio is greater than the Critical F-distribution value, then one may be confident that the individual's genotype or haplotype pair for this particular subset of polymorphic sites in the β₂AR gene is at least partially responsible for, or is at least strongly correlated with the clinical response.

From the analyses described above, a mathematical model may be readily constructed by the skilled artisan that predicts clinical response as a function of β₂AR genotype or haplotype content. Preferably, the model is validated in one or more follow-up clinical trials designed to test the model.

The identification of an association between a clinical response and a genotype or haplotype (or haplotype pair) for the β₂AR gene may be the basis for designing a diagnostic method to determine those individuals who will or will not respond to the treatment, or alternatively, will respond at a lower level and thus may require more treatment, i.e., a greater dose of a drug. The diagnostic method may take one of several forms: for example, a direct DNA test (i.e., genotyping or haplotyping one or more of the polymorphic sites in the β₂AR gene), a serological test, or a physical exam measurement. The only requirement is that there be a good correlation between the diagnostic test results and the underlying β₂AR genotype or haplotype that is in turn correlated with the clinical response. In a preferred embodiment, this diagnostic method uses the predictive haplotyping method described above.

Any or all analytical and mathematical operations involved in practicing the methods of the present invention may be implemented by a computer. In addition, the computer may execute a program that generates views (or screens) displayed on a display device and with which the user can interact to view and analyze large amounts of information relating to the β₂AR gene and its genomic variation, including chromosome location, gene structure, and gene family, gene expression data, polymorphism data, genetic sequence data, and clinical data population data (e.g., data on ethnogeographic origin, clinical responses, genotypes, and haplotypes for one or more populations). The β₂AR polymorphism data described herein may be stored as part of a relational database (e.g., an instance of an Oracle database or a set of ASCII flat files). These polymorphism data maybe stored on the computer's hard drive or may, for example, be stored on a CD ROM or on one or more other storage devices accessible by the computer. For example, the data may be stored on one or more databases in communication with the computer via a network.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLES

The Examples herein are meant to exemplify the various aspects of carrying out the invention and are not intended to limit the scope of the invention in any way. The Examples do not include detailed descriptions for conventional methods employed, such as in the synthesis of oligonucleotides or preparation of antibodies. Such methods are well known to those skilled in the art and are described in numerous publication's, for example, Sambrook, Fritsch, and Maniatis, *Molecular Cloning: a Laboratory Manual, 2ⁿᵈ Edition*, Cold Spring Harbor Laboratory Press, USA, (1989).

Example 1

This example illustrates examination of the β₂AR gene for polymorphic sites from about 1100 base pairs upstream of the ATG start site to about 700 base pairs downstream of the ATG start site.

Amplification of Target Region

Overlapping fragments of the β₂AR gene were amplified from genomic DNA from the Index Repository and the asthma patient cohort, using the following PCR primers, with the indicated positions corresponding to GenBank Accession No. M15169:

Fragment 1

Forward Primer: nt 495–517
Reverse Primer: complement of nt 1735–1708
1241 nt product(495–1735)

Fragment 2

Forward Primer: 1671–1695
Reverse Primer: complement of 2857–2831
1187 nt product (1671–2831)

The resulting PCR products were sequenced using dye terminator chemistry (Big-Dye, PE Biosystems) and an ABI 3700 capillary sequencer. The sequencing primers were designed to provide for overlapping ~500 bp reads.

Analysis of Sequences for Polymorphic Sites

Sequences were analyzed for the presence of polymorphisms using the Polyphred program (Nickerson et al., Nucleic Acids Res. 14:2745–2751, 1997). The presence of a polymorphism was confirmed on both strands. The polymorphisms and their locations in the β₂AR gene are listed in Table 3 below.

TABLE 3

| Polymorphisms Identified in the β₂AR Gene | | | | |
|---|---|---|---|---|
| Polymorphic | Nucleotide Position | | Reference | Variant |
| Site[a] | Figure 1 | Relative to CDS[b] | Allele | Allele |
| PS1 | 565 | −1023 | G | A |
| PS2 | 879 | −709 | C | A |
| PS3 | 934 | −654 | G | A |
| PS4 | 1120 | −468 | G | C |
| PS5 | 1182 | −406 | C | T |
| PS6 | 1221 | −367 | C | T |
| PS7 | 1541 | −47 | C | T |
| PS8 | 1568 | −20 | T | C |
| PS9 | 1633 | 46 | A (Arg) | G (Gly) |
| PS10 | 1666 | 79 | C (Gln) | G (Glu) |
| PS11 | 1839 | 252 | G | A |
| PS12 | 2078 | 491 | C | T |
| PS13 | 2110 | 523 | C | A |

[a]All polymorphic sites other than PS2 and PS5 have been previously reported.
[b]CDS means coding sequence

Example 2

This example illustrates analysis of the β₂AR gene polymorphisms identified in the Index Repository and asthmatic cohort for genotypes and haplotypes.

The different genotypes containing these polymorphisms that were observed in the reference and asthma populations are shown in Table 4 below, with the haplotype pair indicating the combination of haplotypes determined for each individual using the haplotype derivation protocol described below.

TABLE 4

Genotypes and Haplotype Pairs Observed for the β₂-AR gene

| Genotype No. | PS1 | PS2 | PS3 | PS4 | PS5 | PS6 | PS7 | PS8 | PS9 | PS10 | PS11 | PS12 | PS13 | HAP Pair |
|---|---|---|---|---|---|---|---|---|---|---|---|---|---|---|
| 1 | A | C | G | C | C | T | T | T | A | C | G | C | C | 1/1 |
| 2 | A | C | G | G/C | C | C/T | C/T | C/T | A/G | G/C | G | C | C | 1/2 |
| 3 | A/G | C | A/G | C | C | T | T | T | A | C | G | C | C | 1/4 |
| 4 | A/G | C | G | C | C | T | T | T | A/G | C | G/A | C | A/C | 1/6 |
| 5 | A | C | G | C | T/C | T | T | T | A | C | G | C | C | 1/9 |
| 6 | A | C | G | G | C | C | C | C | G | G | G | C | C | 2/2 |
| 7 | A/G | A/C | A/G | G/C | C | C/T | C/T | C/T | A/G | G/C | G | C | C | 2/3 |
| 8 | A/G | C | A/G | G/C | C | C/T | C/T | C/T | A/G | G/C | G | C | C | 2/4 |
| 9 | A/G | C | A/G | G/C | C | C/T | C/T | C/T | G | G/C | G | C | C | 2/5 |
| 10 | A/G | C | G | G/C | C | C/T | C/T | C/T | G | G/C | G/A | C | A/C | 2/6 |
| 11 | A/G | C | G | G/C | C | C/T | C/T | C/T | G | G/C | G/A | C/T | A/C | 2/7 |
| 12 | A/G | C | A/G | G/C | C | C/T | C/T | C/T | A/G | G/C | G/A | C | A/C | 2/8 |
| 13 | A/G | C | G | G/C | C | C/T | C/T | C/T | G | G/C | G/A | C | C | 2/10 |
| 14 | A/G | C | G | G/C | C | C/T | C/T | C/T | G | G/C | G | C | C | 2/11 |
| 15 | G | A/C | A | C | C | T | T | T | A | C | G | C | C | 3/4 |
| 16 | G | C | A | C | C | T | T | T | A | C | G | C | C | 4/4 |
| 17 | G | C | A | C | C | T | T | T | A/G | C | G | C | C | 4/5 |
| 18 | G | C | A/G | C | C | T | T | T | A/G | C | G/A | C | A/C | 4/6 |
| 19 | G | C | A/G | C | C | T | T | T | A/G | C | G/A | C/T | A/C | 4/7 |
| 20 | G | C | A | C | C | T | T | T | A | C | G/A | C | A/C | 4/8 |
| 21 | A/G | C | A/G | C | T/C | T | T | T | A | C | G | C | C | 4/9 |
| 22 | G | C | A/G | C | C | T | T | T | A/G | C | G/A | C | C | 4/10 |
| 23 | A/G | C | A | G/C | C | T | C/T | T | A | C | G | C | C | 4/12 |
| 24 | G | C | G | C | C | T | T | T | G | C | A | C | A | 6/6 |
| 25 | G | C | G | C | C | T | T | T | G | C | A | C/T | A | 6/7 |
| 26 | A/G | C | G | C | T/C | T | T | T | A/G | C | G/A | C | A/C | 6/9 |
| 27 | G | C | G | C | C | T | T | T | G | C | G/A | C | A/C | 6/11 |

*Homozygous positions are indicated by one nucleotide; heterozygous positions are indicated by two nucleotides.

The haplotype pairs shown in the Table 4 were estimated from the unphased genotypes using extension of Clark's algorithm (Clark, A. G. (1990) *Mol Bio Evol* 7, 111–122), in which haplotypes are assigned directly from individuals who are homozygous at all sites or heterozygous at no more than one of the variable sites. This list of haplotypes is then used to deconvolute the unphased genotypes in the remaining (multiply heterozygous) individuals. In our analysis the list of haplotypes was augmented with haplotypes obtained from three families (two multi-generation Caucasian families, one two-generation African-American family).

Following this derivation protocol, the individual haplotypes and their frequencies in the different population groups in the Index Repository and asthmatic cohort were determined and are set forth in Table 5 below.

TABLE 5

β₂AR haplotypes and haplotype frequencies

| HAP No. | Polymorphic Site | | | | | | | | | | | | | Frequency (%)* | | | |
|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | CA | AA | AS | HL |
| 1 | A | C | G | C | C | T | T | T | A | C | G | C | C | 0.7 | 25.0 | 12.5 | 10.0 |
| 2 | A | C | G | G | C | C | C | C | G | G | G | C | C | 48.3 | 6.3 | 10.0 | 26.7 |
| 3 | G | A | A | C | C | T | T | T | A | C | G | C | C | 0.7 | 0.0 | 0.0 | 0.0 |
| 4 | G | C | A | C | C | T | T | T | A | C | G | C | C | 33.0 | 29.7 | 45.0 | 40.0 |
| 5 | G | C | A | C | C | T | T | T | G | C | G | C | C | 1.4 | 0.0 | 0.0 | 0.0 |
| 6 | G | C | G | C | C | T | T | T | G | C | A | C | A | 13.2 | 31.3 | 30.0 | 13.3 |
| 7 | G | C | G | C | C | T | T | T | G | C | A | T | A | 1.0 | 1.6 | 0.0 | 3.3 |
| 8 | G | C | A | C | C | T | T | T | A | C | A | C | A | 0.7 | 0.0 | 0.0 | 0.0 |
| 9 | A | C | G | C | T | T | T | T | A | C | G | C | C | 0.0 | 4.7 | 0.0 | 0.0 |
| 10 | G | C | G | C | C | T | T | T | G | C | A | C | C | 0.7 | 0.0 | 0.0 | 3.3 |
| 11 | G | C | G | C | C | T | T | T | G | C | G | C | C | 0.3 | 0.0 | 2.5 | 0.0 |
| 12 | A | C | G | G | C | T | T | T | A | C | G | C | C | 0.0 | 1.6 | 0.0 | 3.3 |
| | | | | | | | | | | | | | | 100 | 100 | 100 | 100 |

* CA = Caucasian; AA = African-American; AS = Asian; HL = Hispanic-Latinos

The inventors discovered that 13 variable sites exist in the β₂AR, all within a span of 1.6 kb (FIG. 1; Table 3). Two SNPs, at −709 (PS2) and −406 (PS5), have not been previously reported. Of the $2^{13}$ (=8,192) possible combinations of these SNPs, only 12 were found in individuals from the index repository and the asthmatic cohort (Table 5). All SNPs and haplotypes were found to be in conformance with Hardy-Weinberg equilibrium, with the exception of homozygotes for haplotype 1 in Hispanic Latinos, due to the existence of a single homozygote in this population for an otherwise rare haplotype. Four of the observed haplotypes occur in all populations sampled, although at markedly different frequencies. Haplotype 2, the most frequent in Caucasians (48%) is only seen at frequencies of 6%, 10%, and 27% in samples of African-Americans, Asians, and Hispanic Latinos, respectively. Furthermore, this particular haplotype is by far the most distinctive at the nucleotide level, having unique differences at four sites from all other haplotypes sampled. The distribution of haplotype 1 also indicates population differentiation at this locus with a >20 fold lower frequency in Caucasians compared to the other groups. Also, haplotype 6 is more common in African-Americans and Asians compared to the other two groups. In contrast to the above, the frequency of haplotype 4 is similar in all groups. Assigning haplotypes from unphased genotype data from 200 individuals using the above derivation protocol gave the same results as molecular haplotyping except in a single subject due to a discrepancy at one SNP position (data not shown).

Example 3

This example illustrates phylogenetic analysis and linkage disequilibrium analysis of the individual $\beta_2AR$ haplotypes shown in Table 5.

This analysis used a variation of the minimal spanning network algorithm (Excoffier, L., et al., (1992) *Genetics* 131, 479–491.). An advantage of this algorithm over other methods is that it does not force a strictly bifurcating tree as a result. Thus, actual reticulations in the "tree", such as those arising from evolutionary recombination among the haplotypes, can be visualized and interpreted. With this approach every haplotype is connected to the haplotype(s) most similar to itself and the results are shown in FIG. 3.

This phylogenetic analysis of the $\beta_2AR$ haplotypes revealed a deep divergence of haplotype 2 as well as potential evolutionary recombination events. Haplotype 12 appears to be a recombinant between haplotypes 1 and 2.

Also, haplotype 8 is best explained as a recombination between the highly frequent haplotypes 4 and 6.

Figure 4:
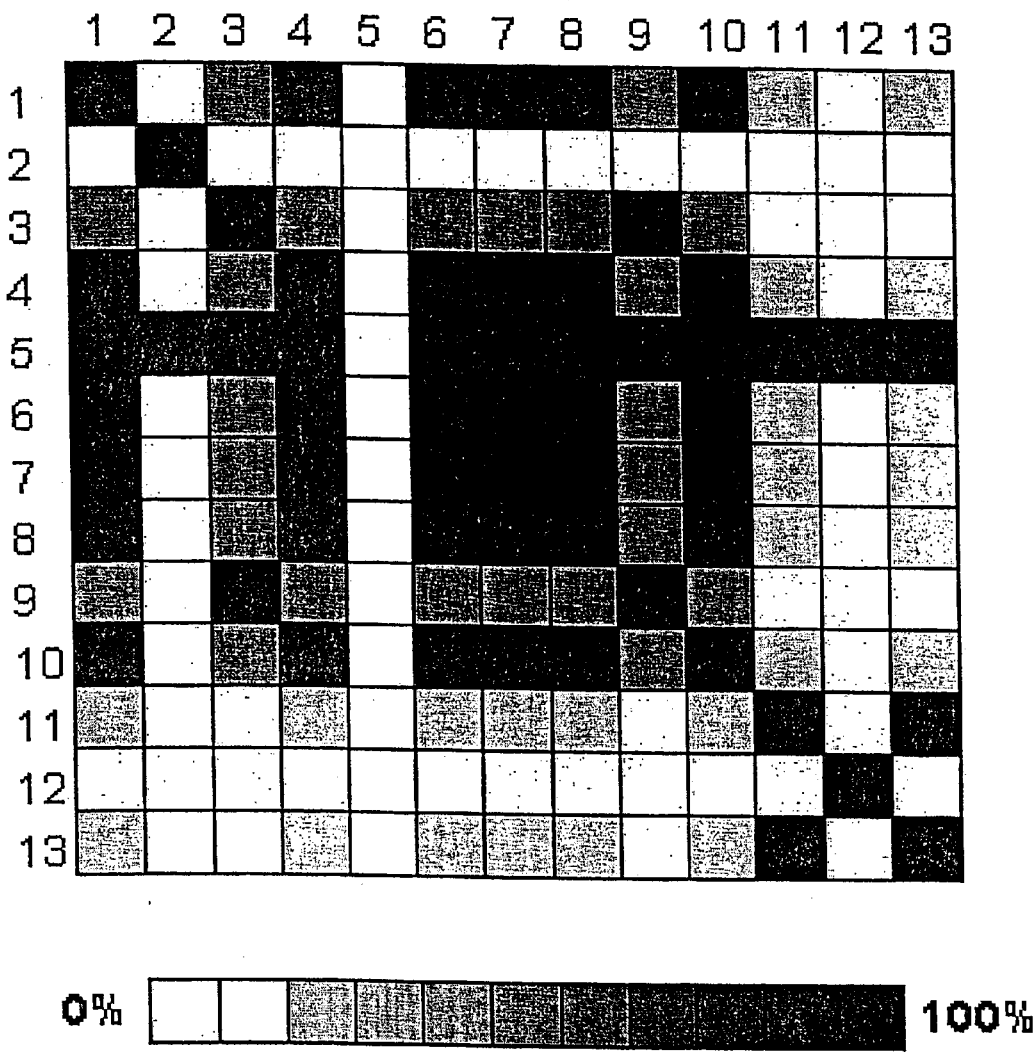
FIG. 4 illustrates the linkage disequilibrium between thirteen polymorphic sites in the $\beta_2AR$ gene with the degree of linkage indicated by shading.

Linkage disequilibrium (Δ) for our largest sample, Caucasians, was quantitated using standard methodology (Hill, W. G., et al., *Theor Appl Genet* 38, 226–231; Hill, W. G. & Weir, B. S. (1994) *Am J Hum Genet* 54, 705–714) and the results are shown in FIG. 4. Although many of the sites are in strong disequilibrium, it is clear that some pairs of close sites have reduced levels of linkage disequilibrium relative to more distantly spaced pairs of sites. This illustrates the hazards inherent in randomly selecting an individual SNP as a surrogate marker. Furthermore, no individual SNP adequately predicted these complex haplotypes.

Example 4

This example illustrates analysis of the $\beta_2AR$ haplotypes in Table 5 for association with asthma patients' response to albuterol.

The patients in the asthma cohort were enrolled from an outpatient facility as described in detail elsewhere (Yan, L., Galinsky, R. E., Bernstein, J. A., Liggett, S. B. & Weinshilboum, R. M. (1999) *Pharmacogenetics* in Press). Patients underwent spirometry before and 30 min after inhalation of 180 μg albuterol delivered by nebulization. Forced expiratory volume in 1 second ($FEV_1$) and forced vital capacity (FVC) were determined in triplicate. The predicted values for these measurements were calculated based on standard algorithms (Morris, J. F., Koski, A. & Johnson, L. C. (1971) *Am Rev Respir Dis* 103, 57–67). The change in the % predicted $FEV_1$ was considered the primary measure of responsiveness to albuterol (Dales, R. E., Spitzer, W. O., Tousignant, P., Schechter, M. & Suissa, S. (1988) *Am Rev Respir Dis* 138, 317–320).

In the Caucasian members of the asthmatic cohort, the two rare SNPs at −709 and −406 were not found. (For purposes of consistency the haplotypes discussed below continue to list these positions although they were invariant in the Caucasian population group in this cohort.) No other differences were found in the frequencies of the haplotypes between the Index Repository and the asthmatic population. The haplotypes were assembled as pairs, and the eighteen haplotype pairs that were found in the asthmatic cohort are shown in Table 6 below.

TABLE 6

Haplotype Pairs Observed in Asthma Patients

| Hap Pair | Chromosome A Polymorphic Sites | | | | | | | | | | | | | Chromosome B Polymorphic Sites | | | | | | | | | | | | | N | % |
|---|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 1 | 2 | 3 | 4 | 5 | 6 | 7 | 8 | 9 | 10 | 11 | 12 | 13 | | |
| 2/4 | A | C | G | G | C | C | C | C | G | G | G | C | C | G | C | A | C | C | T | T | T | A | C | G | C | C | 37 | 30.6 |
| 2/2 | A | C | G | G | C | C | C | C | G | G | G | C | C | A | C | G | G | C | C | C | C | G | G | G | C | C | 25 | 20.7 |
| 2/6 | A | C | G | G | C | C | C | C | G | G | G | C | C | G | C | G | C | C | T | T | T | G | C | A | C | A | 22 | 18.2 |
| 4/4 | G | C | A | C | C | T | T | T | A | C | G | C | C | G | C | A | C | C | T | T | T | A | C | G | C | C | 14 | 11.6 |
| 4/6 | G | C | A | C | C | T | T | T | A | C | G | C | C | G | C | G | C | C | T | T | T | G | C | A | C | A | 8 | 6.6 |
| 2/5 | A | C | G | G | C | C | C | C | G | G | G | C | C | G | G | A | C | C | T | T | T | G | C | G | C | C | 2 | 1.7 |
| 4/10 | G | C | A | C | C | T | T | T | A | C | G | C | C | G | C | G | C | C | T | T | T | G | C | A | C | C | 2 | 1.7 |
| 1/4 | A | C | G | C | C | T | T | T | A | C | G | C | C | G | C | A | C | C | T | T | T | A | C | G | C | C | 1 | 0.8 |
| 1/6 | A | C | G | C | C | T | T | T | A | C | G | C | C | G | C | G | C | C | T | T | T | G | C | A | C | A | 1 | 0.8 |
| 2/11 | A | C | G | G | C | C | C | C | G | G | G | C | C | G | C | G | C | C | T | T | T | C | G | G | C | C | 1 | 0.8 |
| 2/3 | A | G | C | G | C | C | C | C | G | G | G | C | C | G | A | A | C | C | T | T | T | A | C | G | C | C | 1 | 0.8 |
| 2/7 | A | C | G | G | C | C | C | C | G | G | G | C | C | G | C | G | C | C | T | T | T | G | C | A | T | A | 1 | 0.8 |
| 2/8 | A | G | G | G | C | C | C | C | G | G | G | C | C | G | C | A | C | C | T | T | T | A | C | A | C | A | 1 | 0.8 |
| 3/4 | G | A | A | C | C | T | T | T | A | C | G | C | C | G | C | A | C | C | T | T | T | A | C | G | C | C | 1 | 0.8 |
| 4/5 | G | C | A | C | C | T | T | T | A | C | G | C | C | G | C | A | C | C | C | T | T | G | C | G | C | C | 1 | 0.8 |
| 4/7 | G | C | A | C | C | T | T | T | A | C | G | C | C | G | C | G | C | C | T | T | T | G | C | A | T | A | 1 | 0.8 |
| 4/8 | G | C | A | C | C | T | T | T | A | C | G | C | C | G | C | A | C | C | T | T | T | A | C | A | C | A | 1 | 0.8 |
| 6/7 | G | C | G | C | C | T | T | T | G | C | A | C | A | G | C | G | C | C | T | T | T | G | C | A | T | A | 1 | 0.8 |

Eighty-seven percent of the asthmatic cohort are represented by the five most common haplotype pairs. The association between changes in % predicted $FEV_1$ and haplotype pair was assessed by fitting an analysis of covariance model (ANCOVA) with terms for haplotype pair, sex and baseline severity. P-values from pairwise comparisons by haplotype pair were adjusted for multiple comparisons by applying the Holm-Sidak step-down procedure (Ludbrook, J. (1998) *Clin and Exp Pharmacology & Physiology* 25, 1032–1037.). Haplotypes observed in <1% of the cohort that were single nucleotide derivatives of another, more frequent, haplotype were collapsed into the more frequent haplotype if the single nucleotide difference was unique to the rare haplotype. And, for purposes of analysis, the final data set excluded haplotype pairs that were observed in <5% of the cohort. In addition, the African-American asthma patients were excluded from the analysis due to the low number of individuals in this population group. For the analysis of individual SNPs, a similar ANCOVA model was employed with a discrete term for SNP genotype, and terms for sex and baseline severity. The Holm-Sidak step-down procedure was used to adjust the p-values from the individual SNP analyses for the number of tests performed.

Figure 5:
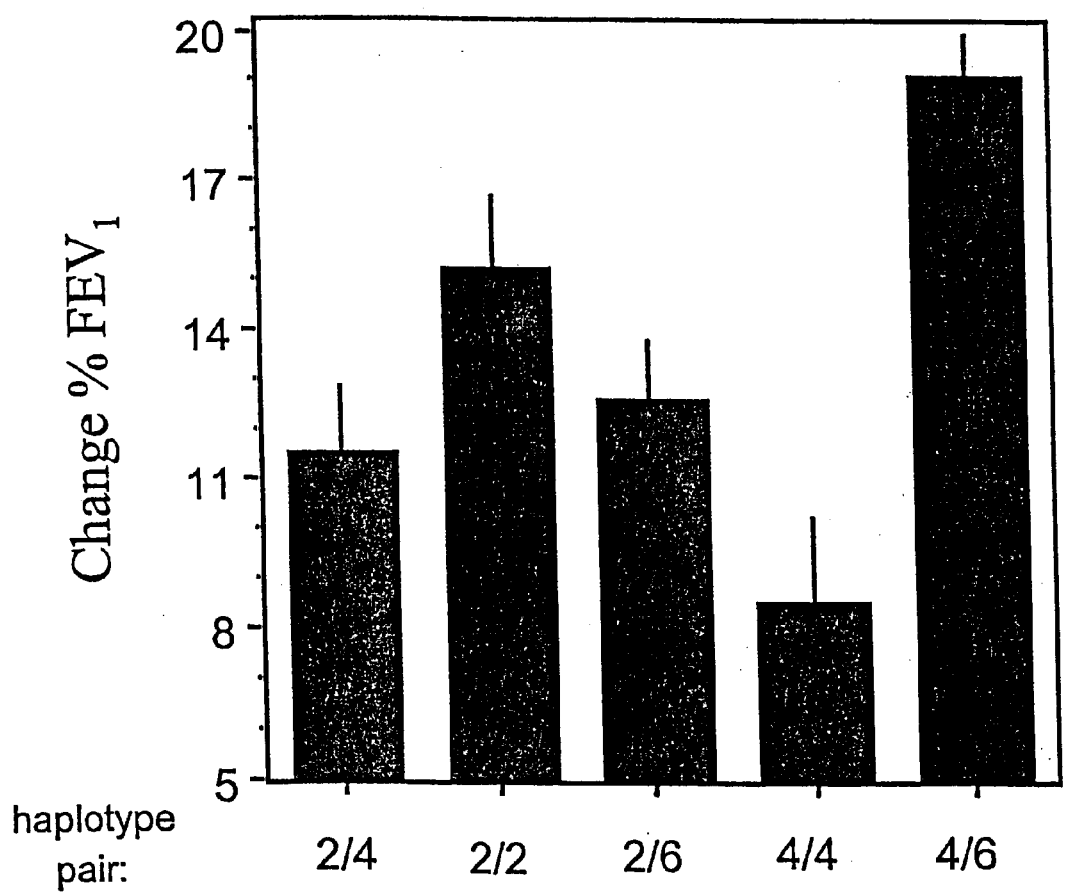
FIG. 5 shows a bar graph of the in vivo $FEV_1$ responses to albuterol exhibited by asthma patients having the indicated haplotype pairs.

The responsiveness to the β-agonist albuterol for Caucasian individuals with the five common haplotype pairs is shown in FIG. 5. Haplotype pair was significantly related to improvements in % $FEV_1$ (p value=0.007 from ANCOVA). To delineate which pairs differ from one another comparisons were made for haplotype pair 4/4 (which had the lowest response) and haplotype pair 4/6 (which had the highest response), versus the other haplotype pairs. Pairwise tests were made while correcting for multiple comparisons. These results showed that the differences of the responses of those with haplotype pairs 4/4 and 4/6 were highly significant (change % $FEV_1$=8.53±1.78 vs 19.1±2.79, p=0.008). Differences were also found between those with pairs 2/4 vs 4/6, and 2/2 vs 4/4 (p=0.036 and 0.046, respectively). In contrast to these results with haplotypes, we found no association between the response to albuterol and any individual SNP. For this analysis, a similar ANCOVA model as above was utilized. The p values for each SNP were all substantially >0.05 (adjusted for multiple comparisons). Based on this in vivo data, it appears that haplotype 4 is associated with depressed responsiveness and haplotype 2 with increased responsiveness. Since 0, 1 or 2 copies of these two haplotypes are present in our population as haplotype pairs 2/2, 2/4 and 4/4, a potential gene dose effect can be assessed by regression analysis. Such an analysis indeed showed a significant relationship between copy number of haplotype 2 (or 4) and the response to albuterol (p=0.009).

The report by Martinez et al, supra, examined response to albuterol and individual polymorphisms at position 46 (Gly or Arg16) or 79 (Glu or Gln27) in a group consisting of normal, "wheezy", and asthmatic children (10.8±0.6 years of age). One hundred eighty eight subjects had both parents being Caucasian, 40 had one parent being Hispanic and 41 had both parents being Hispanic. Only 14% of the subjects had asthma. This study reports an association (p=0.05 for trend) between the Arg16 allele (adenine at nucleic acid 46, PS9 of Table 3) and the prevalence of bronchodilator responsiveness in asthmatics. This analysis did not utilize haplotypes at the two loci. However, this previous finding with the individual polymorphism at PS9 is opposite to what the inventors herein found regarding this site within haplotype pairs 2/2 and 4/4. That is, within these haplotypes guanine at PS9 is associated with the greater bronchodilator response to albuterol, not adenine. Moreover, the very small number of homozygous Arg16 asthmatics (5) who had a positive bronchodilator response, the p value of 0.05, the potential confoundment of race, and the use of mild pediatric asthmatics, makes the Martinez et al. study incomparable to the inventor's study described herein, which utilized multi-site haplotypes, a greater number of asthmatics, and adult Caucasian subjects having a range of asthma severity. Thus, those skilled in the art would not be able to predict from the Martinez et al. study the results of the haplotype study discussed herein.

Two other studies reported limited (2 site) $β_2AR$ haplotypes and some association with asthma, neither of which were related to the bronchodilator response to albuterol. In one study Weir et al., *Am J Resp Crit Care Med* 158:787–791, 1998) the relationship between haplotype encompassing only PS9 and PS10 and asthma death/near death and severity was examined. Death/near death was not associated with a haplotype, although the more moderate asthmatics were more likely to have the Gly16/Gln27 haplotype than mild asthmatics. Those skilled in the art would not be able to predict from this study of two polymorphic sites our results involving multisite haplotypes and the bronchodilating response to albuterol. In another study (D'Amato et al., *Am J Resp Crit Care Med* 158:1968–1973, 1998) haplotypes at PS9 and PS10 were examined for any relationship to bronchial hyperreactivity. Bronchial hyperreactivity is the constriction of the airways during inhalation of certain bronchospastic agents such as methacholine. It is not a test for the relaxation (bronchodilating) response to a β-agonist such as albuterol. In D'Amato et al., the Gly16/Glyn27 haplotype was associated with bronchial hyperreactivity to the inhaled bronchoconstrictor methacholine. Those skilled in the art would not be able to predict from this prior study the relationship between a 13 site $_2A$ haplotype and the response to the bronchodilator albuterol.

The inventors also performed regression calculations to determine the minimal number of polymorphisms that predict association between β2AR polymorphisms and response to albuterol. The regression placed individuals in the clinical cohort into groups having 0, 1, or 2 copies of a haplotype or SNP. It then calculated the significance (reported as a p-value) of the regression line connecting number of copies of the haplotype with response (change in % FEV1). Each site was tested independently to find even marginal association (p<0. 1). Any pair, triple, etc. of sites that showed this nominal association were further combined into haplotypes (sub-haplotypes). A p-value was calculated for the association between each sub-haplotype with response/non-response. A haplotype containing n sites was discarded if there was an m-site haplotype with a greater association (smaller p-value) if m<n. In other words, we favor the simplest association or explanation of the effect, and reject more complex associations. The most significant association was found with the 3-site haplotype comprised of polymorphic sites 3, 9, and 11.

Example 5

This example illustrates analysis of the amount of in vitro expression of two of the predictive $β_2AR$ haplotype pairs.

Figure 6:
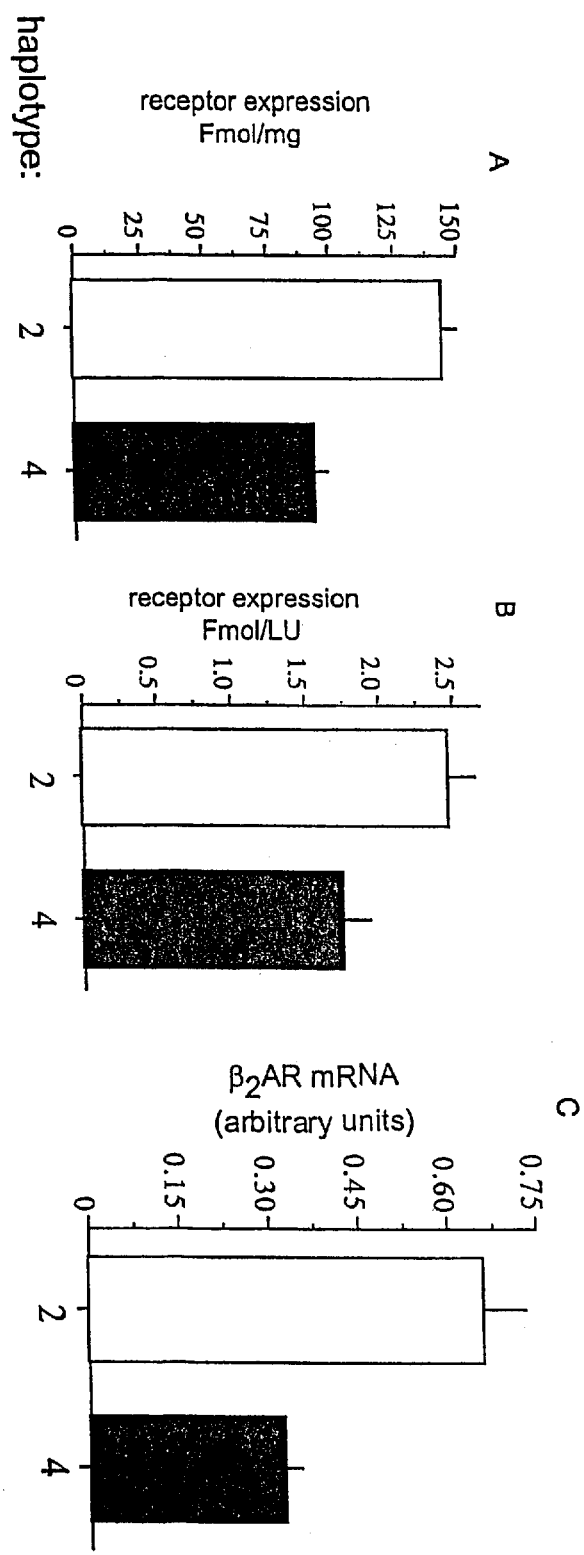
FIG. 6A shows a bar graph illustrating the amount of $\beta_2AR$ protein expression in HEK293 cells co-transfected with a vector containing the indicated $\beta_2AR$ isogene and a luciferase construct.
FIG. 6B shows a bar graph illustrating the amount of $\beta_2AR$ protein expression from FIG. 6A after correction for transfection efficiency as quantitated by luciferase activity.
FIG. 6C shows a bar graph of $\beta_2AR$ mRNA expression in the transfected HEK293 cells of FIG. 6A.

The two homozygous haplotype pairs, 4/4 and 2/2, were common in the asthmatic cohort and displayed significant differences in the in vivo response to the agonist albuterol. To determine whether the SNPs within these two haplotypes result in different levels of $β_2AR$ mRNA or protein expression, transfection studies were carried out in the human embryonic kidney cell line HEK293. These cells were chosen because of their high transfection efficiency, their human origin, and the fact that they express $\beta_2AR$ (~10 fmol/mg) and thus presumably have the relevant transcription factors for expression of the human gene. PCR products of the $\beta_2AR$ gene representing haplotypes 2 and 4 were derived from human genomic DNA, subcloned into pCR2.1 and the sequence verified. The pCR2.1 vector lacks a eukaryotic responsive promoter and thus the expression of the $\beta_2AR$ gene in mammalian cells is directed by the included $\beta_2AR$ promoter sequence. HEK293 cells were transfected using a lipofectamine method (Gene Therapy Systems, San Diego, Calif.). Cells were transfected with 10 $\mu g$ $\beta_2AR$ plasmid, 2 $\mu g$ luciferase plasmid, and 50 $\mu l$ of lipofectamine reagent. Two days later cells were harvested for radioligand binding, mRNA studies; and luciferase activity as previously described (McGraw, D. W., Forbes, S. L., Kramer, L. A. & Liggett, S. B. (1998) *J Clin Invest* 102, 1927–1932.). Briefly, cells were washed three times in phosphate buffered saline, lysed in hypotonic 5 mM Tris, 2 mM EDTA pH 7.40 buffer, and the particulates centrifuged at 40,000×g for 10 min. Receptor expression was determined by radioligand binding using 400 pM $^{125}$I-cyanopindolol ($^{125}$I-CYP). Non-specific binding was determined in the presence of 1 $\mu M$ propranolol. As might be expected, the levels of expression using the $\beta_2AR$ promoter were significantly less than what has previously been reported with viral promoters (Tepe, N. M. & Liggett, S. B. (2000) *J Receptor & Signal Transduction Res* 20, 75–85). Nevertheless, the levels obtained (~100 fmol/mg receptor by radioligand binding) were clearly above background and in fact are similar to $\beta_2AR$ expression in the lung (Green, S. A., Turki, J., Bejarano, P., Hall, I. P. & Liggett, S. B. (1995) *Am J Resp Cell Mol Biol* 13, 25–33). Luciferase activity of cell lysates was determined using a commercial assay (Promega) and was used to control for minor differences in transfection efficiency from plate to plate. $\beta_2AR$ density is thus expressed as fmol/mg membrane protein or fmol/light unit (fmol/LU) as previously described (McGraw et al., supra). mRNA levels were determined using ribonuclease protection assays with a 563 bp antisense riboprobe corresponding to the most 3' region of the $\beta_2AR$ ORF as described previously (McGraw, D. W., Forbes, S. L., Witte, D. P., Fortner, C. N., Paul, R. J. & Liggett, S. B. (1999) *J Biol Chem* 274, 32241–32247). $\beta$-actin mRNA was simultaneously quantitated confirming the equivalent loading of the samples. The results of these experiments are shown in FIG. 6.

As shown in FIG. 6A, the level of expression was clearly different between $\beta_2AR$ isogenes defined by haplotypes 2 and 4. When the construct defined by haplotype 2 was utilized, $\beta_2AR$ expression was 144±12.8 fmol/mg compared to 93.6±5.7 fmol/mg when the haplotype 4 construct was used (p<0.005). When corrected for transfection efficiency by quantitating luciferase activity derived from co-expression of a luciferase construct, the differences in expression of the $\beta_2AR$ (fmol/LU) between the two haplotypes remained (FIG. 6B). Similarly the $\beta_2AR$ mRNA levels as determined by quantitative RNAse protection assays were consistently higher for the haplotype 2-transfected cells than $\beta_2AR$ mRNA levels in the haplotype 4-transfected cells (0.663±0.067 vs 0.320±0.024 arbitrary units, p<0.005) (FIG. 6C). The above results for both protein and mRNA expression are entirely consistent with the in vivo findings, where individuals with haplotype pair 2/2 had a ~50% greater response than those with haplotype pair 4/4 (FIG. 5).

Comparisons of the sequence of haplotypes 2 and 4 reveal eight differences in the thirteen SNP positions. These include differences in amino acid 19 of the BUP, and amino acids 16 and 27 of the receptor protein. Each of these, studied in isolation, have been shown to alter expression or trafficking of the receptor (Green, S., Turki, J., Innis, M. & Liggett, S. B. (1994) *Biochem* 33, 9414–9419; McGraw, D. W., Forbes, S. L., Kramer, L. A. & Liggett, S. B. (1998) *J Clin Invest* 102, 1927–1932), but the effects of the various SNP combinations at these loci have not previously been explored. Interestingly, based on previous work with the BUP SNP (PS7) studied in isolation, the skilled artisan would have predicted that the T allele would be associated with higher expression. This was evaluated, however, within the context of the Gly16 (G at PS9) and Glu27 (G at PS10) alleles, which as shown in Table 5 were never found in combination with T at PS7. This emphasizes the importance of studying polymorphisms in vitro within the context of a validated haplotype.

The SNPs at the other five loci that differ between haplotypes 2 and 4 are at PS1, PS3, PS4, PS6 and PS8. A database search for transcription factor binding sites (Heinemeyer, T., Chen, X., Karas, H., Kel, A. E., Kel, O. V., Liebich, I., Meinhardt, T., Reuter, I., Schacherer, F. & Wingender, E. (1999) *Nucleic Acids Res* 27, 318–322) shows that these SNPs are located within, or closely flank, a number of potential cis-acting elements. For example, PS1 flanks potential binding sites for AP-4 and C/EBP; PS3 and PS4 each flank an NF-1 consensus sequence; and PS 6 is within a CP2 consensus sequence. Of note, the synonymous SNP at PS13 which has been associated with altered responsiveness to albuterol in Japanese families (Ohe, M., Munakata, M., Hizawa, N., Itoh, A., Doi, I., Yamaguchi, E., Homma, Y. & Kawakami, Y. (1995) *Thorax* 50, 353–359.) was invariant between haplotypes 2 and 4. However, this SNP along with the SNP at PS11 distinguishes one common haplotype (haplotype 6) from the other common haplotypes. And, haplotype 6 appears to have some effect on response (FIG. 5).

Whether a smaller subset of $\beta_2AR$ SNPs defines the cellular expression phenotype cannot be ascertained from the current molecular approach since this would require systematic construction of vectors representing many unique haplotypes. Since a large fraction of these would in fact be rare (or never found) in the human population, the inventors have taken the approach of restricting our examination to the common haplotypes, since ultimately these are most relevant to pharmacogenetics. However, based on the results of the current in vivo responsiveness studies, the cell transfection experiments, and previous studies with isolated SNPs, it is likely that the biologic phenotype is directed by an interaction involving transcription, translation and protein processing that ultimately defines the effect of these haplotypes.

In summary, the inventors identified thirteen polymorphic sites in a contiguous region of the 5' upstream and coding sequence of the $\beta_2AR$ in humans. Twelve distinct haplotypes were represented in a population of four major ethnic groups. Several relatively recent recombination events appear to be responsible for some haplotypes. A striking divergence in ethnic distribution was found for several haplotypes. Five haplotype pairs were common in asthmatics, and there were clear differences in the in vivo response to a $\beta_2AR$ agonist based on haplotype pair. In contrast, no isolated SNP had any predictive utility. The homozygous haplotypes 2/2 and 4/4 with divergent agonist efficacies were shown to have differential effects on $\beta_2AR$ gene and protein expression in vitro, consistent with the direction and magnitude of the in vivo responses.

In view of the above, it will be seen that the several advantages of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

All references cited in this specification, including patents and patent applications, are hereby incorporated in their entirety by reference. The discussion of references herein is intended merely to summarize the assertions made by their authors and no admission is made that any reference constitutes prior art. Applicants reserve the right to challenge the accuracy and pertinency of the cited references.

What is claimed is:

1. A diagnostic kit for predicting an individual's bronchodilating response to a β-agonist comprising a set of genotyping oligonucleotides, wherein said set comprises a first oligonucleotide for genotyping PS3, a second oligonucleotide for genotyping PS9 and a third oligonucleotide for genotyping PS11 in the $\beta_2$AR gene packaged in a container, wherein PS3 is located in the $\beta_2$AR gene at a nucleotide position corresponding to nucleotide 934 in SEQ ID NO:1, PS9 is located in the $\beta_2$AR gene at a nucleotide position corresponding to nucleotide 1633 in SEQ ID NO:1, and PS11 is located in the $\beta_2$AR gene at a nucleotide position corresponding to nucleotide 1839 in SEQ ID NO;1, wherein each of the first, second and third oligonucleotides is selected from the group consisting of an allele specific oligonucleotide probe, an allele specific oligonucleotide primer, and a primer extension oligonucleotide.

2. The kit of claim 1, wherein the set of genotyping oligonucleotides consists of a first primer extension oligonucleotide for genotyping PS3, a second primer extension oligonucleotide for genotyping PS9, and a third primer extension oligonucleotide for genotyping PS11.

3. The kit of claim 1, wherein the set of genotyping oligonucleotides further comprises oligonucleotides for genotyping one or more additional $\beta_2$AR polymorphic sites selected from the group consisting of PS1, PS2, PS4, PS5, PS6, PS7, PS8, PS10, PS12 and PS13, wherein PS1 is located in the $\beta_2$AR gene at a nucleotide position corresponding to nucleotide 565 in SEQ ID NO:1, wherein PS2 is located in the $\beta_2$AR gene at a nucleotide position corresponding to nucleotide 879 in SEQ ID NO:1, wherein PS4 is located in the $\beta_2$AR gene at a nucleotide position corresponding to nucleotide 1120 in SEQ ID NO:1, wherein PS5 is located in the $\beta_2$AR gene at a nucleotide position corresponding to nucleotide 1182 in SEQ ID NO:1, wherein PS6 is located in the $\beta_2$AR gene at a nucleotide position corresponding to nucleotide 1221 in SEQ ID NO:1, wherein PS7 is located in the $\beta_2$AR gene at a nucleotide position corresponding to nucleotide 1541 in SEQ ID NO;1, wherein PS8 is located in the β₂AR gene at a nucleotide position corresponding to nucleotide 1568 in SEQ ID NO:1, wherein PS10 is located in the β₂AR gene at a nucleotide position corresponding to nucleotide 1666 in SEQ ID NO:1, wherein PS12 is located in the β₂AR gene at a nucleotide position corresponding to nucleotide 2078 in SEQ ID NO:1, and wherein PS13 is located in the β₂AR gene at a nucleotide position corresponding to nucleotide 2110 in SEQ ID NO:1.

4. The kit of claim 1, wherein the β-agonist is albuterol.

5. A method for predicting an individual's bronchodilating response to a β-agonist, which comprises (a) assigning a β₂AR haplotype pair to the individual, wherein the β₂AR haplotype pair is selected from the group consisting of haplotype pairs 4/6, 2/2, 2/6, 2/4, and 4/4, which are shown in Table 4; and (b) using the assigned haplotype pair to predict the individual's bronchodilating response, wherein assignment of β₂AR haplotype pair 4/6 or 2/2 predicts that the individual will exhibit a greater bronchodilating response than an individual with a β₂AR haplotype pair assignment of 2/6, 2/4, or 4/4, assignment of β₂AR haplotype pair 2/6 predicts that the individual will exhibit a greater bronchodilating response than an individual with a β₂AR haplotype pair assignment of 2/4 or 4/4 and a smaller bronchodilating response than an individual with a β₂AR haplotype pair assignment of 4/6 or 2/2, and assignment of β₂AR haplotype pair 2/4 or 4/4 predicts that the individual will exhibit no bronchodilating response.

6. The method of claim 5, wherein the assigning step comprises determining a genotype for PS3, PS9 and PS11 in the individual's β₂AR gene and using the genotype to assign the haplotype pair.

7. The method of claim 6, wherein the assigning step further comprises determining a genotype for one or more additional polymorphic sites selected from the group consisting of PS1, PS2, PS4, PS5, PS6, PS7, PS8, PS10, PS12 and PS13.

8. The method of claim 5, wherein the β-agonist is albuterol.

9. The kit of claim 1, which further comprises instructions for using the oligonucleotides and assigning a β₂AR haplotype pair from the results, wherein the β₂AR haplotype pair is selected from the group consisting of haplotype pairs 4/6, 2/2, 2/6, 2/4, and 4/4, which are shown in Table 4.

10. The method of claim 5, wherein said individual is of Caucasian descent.

* * * * *

UNITED STATES PATENT AND TRADEMARK OFFICE
CERTIFICATE OF CORRECTION

PATENT NO. : 6,586,183 B2
DATED : July 1, 2003
INVENTOR(S) : Connie M. Drysdale et al.

It is certified that error appears in the above-identified patent and that said Letters Patent is hereby corrected as shown below:

<u>Column 1,</u>
Line 9, please insert the following:
-- GOVERNMENT INTEREST

This invention was made with government support under National Institute of Health Grant RO1 HL45967. The United States government has certain rights in the invention. --

Signed and Sealed this

Twenty-seventh Day of July, 2004

JON W. DUDAS
*Acting Director of the United States Patent and Trademark Office*

SEQUENCE LISTING

<160> NUMBER OF SEQ ID NOS: 18

<210> SEQ ID NO 1
<211> LENGTH: 3451
<212> TYPE: DNA
<213> ORGANISM: Homo sapiens
<220> FEATURE:
<221> NAME/KEY: CDS
<222> LOCATION: (1588)..(2829)

<400> SEQUENCE: 1

```
cccgggttca agagattctc ctgtctcagc ctcccgagta gctgggacta caggtacgtg        60
ccaccacacc tggctaattt ttgtattttt agtagagaca agagttacac catattggcc       120
aggatctttt gctttctata gcttcaaaat gttcttaatg ttaagacatt cttaatactc       180
tgaaccatat gaatttgcca ttttggtaag tcacagacgc cagatggtgg caatttcaca       240
tggcacaacc cgaaagatta acaaactatc cagcagatga aaggattttt tttagtttca       300
ttgggtttac tgaagaaatt gtttgaattc tcattgcatc tccagttcaa cagataatga       360
gtgagtgatg ccacactctc aagagttaaa aacaaaacaa caaaaaaatt aaaacaaaag       420
cacacaactt tctctctctg tcccaaaata catacttgca taccccgct ccagataaaa        480 tccaaagggt aaaactgtct tcatgcctgc aaattcctaa ggagggcacc taaagtactt       540
gacagcgagt gtgctgagga aatcggcagc tgttgaagtc acctcctgtg ctcttgccaa       600
atgtttgaaa gggaatacac tgggttaccg ggtgtatgtt gggaggggag cattatcagt       660
gctcgggtga ggcaagttcg gagtacccag atggagacat ccgtgtctgt gtcgctctgg       720
atgcctccaa gccagcgtgt gtttactttc tgtgtgtgtc accatgtctt tgtgcttctg       780
ggtgcttctg tgtttgtttc tggccgcgtt tctgtgttgg acagggtga ctttgtgccg        840 gatggcttct gtgtgagagc gcgcgcgagt gtgcatgtcg gtgagctggg agggtgtgtc       900
tcagtgtcta tggctgtggt tcggtataag tctgagcatg tctgccaggg tgtatttgtg       960
cctgtatgtg cgtgcctcgg tgggcactct cgtttccttc cgaatgtggg gcagtgccgg      1020
tgtgctgccc tctgccttga gacctcaagc cgcgcaggcg cccagggcag gcaggtagcg      1080
gccacagaag agccaaaagc tcccgggttg gctggtaagg acaccacctc cagctttagc      1140 cctctgggc cagccagggt agccgggaag cagtggtggc ccgccctcca gggagcagtt       1200
gggccccgcc cgggccagcc ccaggagaag gagggcgagg ggaggggagg gaaaggggag      1260
gagtgcctcg cccttcgcg gctgccggcg tgccattggc cgaaagttcc cgtacgtcac       1320
ggcgagggca gttcccctaa agtcctgtgc acataacggg cagaacgcac tgcgaagcgg      1380
cttcttcaga gcacgggctg gaactggcag gcaccgcgag cccctagcac ccgacaagct      1440
gagtgtgcag gacgagtccc caccacaccc acaccacagc cgctgaatga ggcttccagg      1500
cgtccgctcg cggcccgcag agcccgccg tgggtccgcc cgctgaggcg cccccagcca       1560
gtgcgcttac ctgccagact gcgcgcc atg ggg caa ccc ggg aac ggc agc gcc      1614
```

```
                    Met Gly Gln Pro Gly Asn Gly Ser Ala
                     1                   5 ttc ttg ctg gca ccc aat aga agc cat gcg ccg gac cac gac gtc acg    1662
Phe Leu Leu Ala Pro Asn Arg Ser His Ala Pro Asp His Asp Val Thr
 10              15                  20                  25 cag caa agg gac gag gtg tgg gtg gtg ggc atg ggc atc gtc atg tct    1710
Gln Gln Arg Asp Glu Val Trp Val Val Gly Met Gly Ile Val Met Ser
                 30                  35                  40 ctc atc gtc ctg gcc atc gtg ttt ggc aat gtg ctg gtc atc aca gcc    1758
Leu Ile Val Leu Ala Ile Val Phe Gly Asn Val Leu Val Ile Thr Ala
             45                  50                  55 att gcc aag ttc gag cgt ctg cag acg gtc acc aac tac ttc atc act    1806
Ile Ala Lys Phe Glu Arg Leu Gln Thr Val Thr Asn Tyr Phe Ile Thr
         60                  65                  70 tca ctg gcc tgt gct gat ctg gtc atg ggc ctg gca gtg gtg ccc ttt    1854
Ser Leu Ala Cys Ala Asp Leu Val Met Gly Leu Ala Val Val Pro Phe
     75                  80                  85 ggg gcc gcc cat att ctt atg aaa atg tgg act ttt ggc aac ttc tgg    1902
Gly Ala Ala His Ile Leu Met Lys Met Trp Thr Phe Gly Asn Phe Trp
 90              95                 100                 105 tgc gag ttt tgg act tcc att gat gtg ctg tgc gtc acg gcc agc att    1950
Cys Glu Phe Trp Thr Ser Ile Asp Val Leu Cys Val Thr Ala Ser Ile
                110                 115                 120 gag acc ctg tgc gtg atc gca gtg gat cgc tac ttt gcc att act tca    1998
Glu Thr Leu Cys Val Ile Ala Val Asp Arg Tyr Phe Ala Ile Thr Ser
                125                 130                 135 cct ttc aag tac cag agc ctg ctg acc aag aat aag gcc cgg gtg atc    2046
Pro Phe Lys Tyr Gln Ser Leu Leu Thr Lys Asn Lys Ala Arg Val Ile
            140                 145                 150 att ctg atg gtg tgg att gtg tca ggc ctt acc tcc ttc ttg ccc att    2094
Ile Leu Met Val Trp Ile Val Ser Gly Leu Thr Ser Phe Leu Pro Ile
155                 160                 165 cag atg cac tgg tac cgg gcc acc cac cag gaa gcc atc aac tgc tat    2142
Gln Met His Trp Tyr Arg Ala Thr His Gln Glu Ala Ile Asn Cys Tyr
170                 175                 180                 185 gcc aat gag acc tgc tgt gac ttc ttc acg aac caa gcc tat gcc att    2190
Ala Asn Glu Thr Cys Cys Asp Phe Phe Thr Asn Gln Ala Tyr Ala Ile
                190                 195                 200 gcc tct tcc atc gtg tcc ttc tac gtt ccc ctg gtg atc atg gtc ttc    2238
Ala Ser Ser Ile Val Ser Phe Tyr Val Pro Leu Val Ile Met Val Phe
            205                 210                 215 gtc tac tcc agg gtc ttt cag gag gcc aaa agg cag ctc cag aag att    2286
Val Tyr Ser Arg Val Phe Gln Glu Ala Lys Arg Gln Leu Gln Lys Ile
            220                 225                 230 gac aaa tct gag ggc cgc ttc cat gtc cag aac ctt agc cag gtg gag    2334
Asp Lys Ser Glu Gly Arg Phe His Val Gln Asn Leu Ser Gln Val Glu
        235                 240                 245 cag gat ggg cgg acg ggg cat gga ctc cgc aga tct tcc aag ttc tgc    2382
Gln Asp Gly Arg Thr Gly His Gly Leu Arg Arg Ser Ser Lys Phe Cys
250                 255                 260                 265 ttg aag gag cac aaa gcc ctc aag acg tta ggc atc atc atg ggc act    2430
Leu Lys Glu His Lys Ala Leu Lys Thr Leu Gly Ile Ile Met Gly Thr
                270                 275                 280 ttc acc ctc tgc tgg ctg ccc ttc ttc atc gtt aac att gtg cat gtg    2478
Phe Thr Leu Cys Trp Leu Pro Phe Phe Ile Val Asn Ile Val His Val
                285                 290                 295 atc cag gat aac ctc atc cgt aag gaa gtt tac atc ctc cta aat tgg    2526
Ile Gln Asp Asn Leu Ile Arg Lys Glu Val Tyr Ile Leu Leu Asn Trp
            300                 305                 310
```

-continued

| | | | | | | | | | | |
|---|---|---|---|---|---|---|---|---|---|---|
| ata | ggc | tat | gtc | aat | tct | ggt | ttc | aat | ccc | ctt | atc | tac | tgc | cgg | agc | 2574 |
| Ile | Gly | Tyr | Val | Asn | Ser | Gly | Phe | Asn | Pro | Leu | Ile | Tyr | Cys | Arg | Ser | |
| | 315 | | | | 320 | | | | 325 | | | | | | | |

```
ata ggc tat gtc aat tct ggt ttc aat ccc ctt atc tac tgc cgg agc      2574
Ile Gly Tyr Val Asn Ser Gly Phe Asn Pro Leu Ile Tyr Cys Arg Ser
    315                 320                 325 cca gat ttc agg att gcc ttc cag gag ctt ctg tgc ctg cgc agg tct      2622
Pro Asp Phe Arg Ile Ala Phe Gln Glu Leu Leu Cys Leu Arg Arg Ser
330                 335                 340                 345 tct ttg aag gcc tat ggg aat ggc tac tcc agc aac ggc aac aca ggg      2670
Ser Leu Lys Ala Tyr Gly Asn Gly Tyr Ser Ser Asn Gly Asn Thr Gly
            350                 355                 360 gag cag agt gga tat cac gtg gaa cag gag aaa gaa aat aaa ctg ctg      2718
Glu Gln Ser Gly Tyr His Val Glu Gln Glu Lys Glu Asn Lys Leu Leu
        365                 370                 375 tgt gaa gac ctc cca ggc acg gaa gac ttt gtg ggc cat caa ggt act      2766
Cys Glu Asp Leu Pro Gly Thr Glu Asp Phe Val Gly His Gln Gly Thr
    380                 385                 390 gtg cct agc gat aac att gat tca caa ggg agg aat tgt agt aca aat      2814
Val Pro Ser Asp Asn Ile Asp Ser Gln Gly Arg Asn Cys Ser Thr Asn
395                 400                 405 gac tca ctg ctg taa agcagttttt ctacttttaa agaccccccc cccccccaaca    2869
Asp Ser Leu Leu
410
```
gaacactaaa cagactattt aacttgaggg taataaactt agaataaaat tgtaaaaatt 2929 gtatagagat atgcagaagg aagggcatcc ttctgccttt tttatttttt taagctgtaa 2989 aaagagagaa aacttatttg agtgattatt tgttatttgt acagttcagt tcctctttgc 3049 atggaatttg taagtttatg tctaaagagc tttagtccta gaggacctga gtctgctata 3109 ttttcatgac ttttccatgt atctacctca ctattcaagt attagggta atatattgct 3169 gctggtaatt tgtatctgaa ggagattttc cttcctacac ccttggactt gaggattttg 3229 agtatctcgg acctttcagc tgtgaacatg gactcttccc ccactcctct tatttgctca 3289 cacggggtat tttaggcagg gatttgagga gcagcttcag ttgttttccc gagcaaaggt 3349 ctaaagttta cagtaaataa aatgtttgac catgccttca ttgcacctgt ttgtccaaaa 3409 cccccttgact ggagtgctgt tgcctccccc actggaaacc gc 3451

<210> SEQ ID NO 2
<211> LENGTH: 413
<212> TYPE: PRT
<213> ORGANISM: Homo sapiens

<400> SEQUENCE: 2

Met Gly Gln Pro Gly Asn Gly Ser Ala Phe Leu Leu Ala Pro Asn Arg
1               5                   10                  15

Ser His Ala Pro Asp His Asp Val Thr Gln Gln Arg Asp Glu Val Trp
            20                  25                  30

Val Val Gly Met Gly Ile Val Met Ser Leu Ile Val Leu Ala Ile Val
        35                  40                  45

Phe Gly Asn Val Leu Val Ile Thr Ala Ile Ala Lys Phe Glu Arg Leu
    50                  55                  60

Gln Thr Val Thr Asn Tyr Phe Ile Thr Ser Leu Ala Cys Ala Asp Leu
65                  70                  75                  80

Val Met Gly Leu Ala Val Val Pro Phe Gly Ala Ala His Ile Leu Met
                85                  90                  95

Lys Met Trp Thr Phe Gly Asn Phe Trp Cys Glu Phe Trp Thr Ser Ile
            100                 105                 110

Asp Val Leu Cys Val Thr Ala Ser Ile Glu Thr Leu Cys Val Ile Ala
        115                 120                 125

```
Val Asp Arg Tyr Phe Ala Ile Thr Ser Pro Phe Lys Tyr Gln Ser Leu
    130                 135                 140

Leu Thr Lys Asn Lys Ala Arg Val Ile Ile Leu Met Val Trp Ile Val
145                 150                 155                 160

Ser Gly Leu Thr Ser Phe Leu Pro Ile Gln Met His Trp Tyr Arg Ala
                165                 170                 175

Thr His Gln Glu Ala Ile Asn Cys Tyr Ala Asn Glu Thr Cys Cys Asp
                180                 185                 190

Phe Phe Thr Asn Gln Ala Tyr Ala Ile Ala Ser Ser Ile Val Ser Phe
                195                 200                 205

Tyr Val Pro Leu Val Ile Met Val Phe Val Tyr Ser Arg Val Phe Gln
    210                 215                 220

Glu Ala Lys Arg Gln Leu Gln Lys Ile Asp Lys Ser Glu Gly Arg Phe
225                 230                 235                 240

His Val Gln Asn Leu Ser Gln Val Glu Gln Asp Gly Arg Thr Gly His
                245                 250                 255

Gly Leu Arg Arg Ser Ser Lys Phe Cys Leu Lys Glu His Lys Ala Leu
                260                 265                 270

Lys Thr Leu Gly Ile Ile Met Gly Thr Phe Thr Leu Cys Trp Leu Pro
                275                 280                 285

Phe Phe Ile Val Asn Ile Val His Val Ile Gln Asp Asn Leu Ile Arg
                290                 295                 300

Lys Glu Val Tyr Ile Leu Leu Asn Trp Ile Gly Tyr Val Asn Ser Gly
305                 310                 315                 320

Phe Asn Pro Leu Ile Tyr Cys Arg Ser Pro Asp Phe Arg Ile Ala Phe
                325                 330                 335

Gln Glu Leu Leu Cys Leu Arg Arg Ser Ser Leu Lys Ala Tyr Gly Asn
                340                 345                 350

Gly Tyr Ser Ser Asn Gly Asn Thr Gly Glu Gln Ser Gly Tyr His Val
                355                 360                 365

Glu Gln Glu Lys Glu Asn Lys Leu Leu Cys Glu Asp Leu Pro Gly Thr
                370                 375                 380

Glu Asp Phe Val Gly His Gln Gly Thr Val Pro Ser Asp Asn Ile Asp
385                 390                 395                 400

Ser Gln Gly Arg Asn Cys Ser Thr Asn Asp Ser Leu Leu
                405                 410
```

<210> SEQ ID NO 3
<211> LENGTH: 15
<212> TYPE: DNA
<213> ORGANISM: Homo sapiens

<400> SEQUENCE: 3
tgcatgtcgg tgagc                                                  15

<210> SEQ ID NO 4
<211> LENGTH: 15
<212> TYPE: DNA
<213> ORGANISM: Homo sapiens

<400> SEQUENCE: 4
tgcatgtagg tgagc                                                  15

<210> SEQ ID NO 5
<211> LENGTH: 15
<212> TYPE: DNA

```
<400> SEQUENCE: 5
ggtggcccgc cctcc                                                        15

<210> SEQ ID NO 6
<211> LENGTH: 15
<212> TYPE: DNA
<213> ORGANISM: Homo sapiens

<400> SEQUENCE: 6
ggtggcctgc cctcc                                                        15

<210> SEQ ID NO 7
<211> LENGTH: 15
<212> TYPE: DNA
<213> ORGANISM: Homo sapiens

<400> SEQUENCE: 7
cgagtgtgca tgtcg                                                        15

<210> SEQ ID NO 8
<211> LENGTH: 15
<212> TYPE: DNA
<213> ORGANISM: Homo sapiens

<400> SEQUENCE: 8
ctcccagctc accga                                                        15

<210> SEQ ID NO 9
<211> LENGTH: 15
<212> TYPE: DNA
<213> ORGANISM: Homo sapiens

<400> SEQUENCE: 9
cgagtgtgca tgtag                                                        15

<210> SEQ ID NO 10
<211> LENGTH: 15
<212> TYPE: DNA
<213> ORGANISM: Homo sapiens

<400> SEQUENCE: 10
ctcccagctc accta                                                        15

<210> SEQ ID NO 11
<211> LENGTH: 15
<212> TYPE: DNA
<213> ORGANISM: Homo sapiens

<400> SEQUENCE: 11
agcagtggtg gcccg                                                        15

<210> SEQ ID NO 12
<211> LENGTH: 15
<212> TYPE: DNA
<213> ORGANISM: Homo sapiens

<400> SEQUENCE: 12
ctccctggag ggcgg                                                        15

<210> SEQ ID NO 13
<211> LENGTH: 15
<212> TYPE: DNA
<213> ORGANISM: Homo sapiens
```

-continued

```
<400> SEQUENCE: 13
agcagtggtg gcctg                                                  15

<210> SEQ ID NO 14
<211> LENGTH: 15
<212> TYPE: DNA
<213> ORGANISM: Homo sapiens

<400> SEQUENCE: 14
ctccctggag ggcag                                                  15

<210> SEQ ID NO 15
<211> LENGTH: 10
<212> TYPE: DNA
<213> ORGANISM: Homo sapiens

<400> SEQUENCE: 15
gtgtgcatgt                                                        10

<210> SEQ ID NO 16
<211> LENGTH: 10
<212> TYPE: DNA
<213> ORGANISM: Homo sapiens

<400> SEQUENCE: 16
ccagctcacc                                                        10

<210> SEQ ID NO 17
<211> LENGTH: 10
<212> TYPE: DNA
<213> ORGANISM: Homo sapiens

<400> SEQUENCE: 17
agtggtggcc                                                        10

<210> SEQ ID NO 18
<211> LENGTH: 10
<212> TYPE: DNA
<213> ORGANISM: Homo sapiens

<400> SEQUENCE: 18
cctggagggc                                                        10
```